US011439148B2

(12) United States Patent
Thomson et al.

(10) Patent No.: US 11,439,148 B2
(45) Date of Patent: Sep. 13, 2022

(54) PYRIMIDINE DERIVATIVES

(71) Applicant: SYNGENTA PARTICIPATIONS AG, Basel (CH)

(72) Inventors: Niall Rae Thomson, Bracknell (GB); Gordon Alastair Bell, Bracknell (GB); Philip Taylor, Bracknell (GB); Julia Lynne Ramsay, Bracknell (GB); Stephanie Lucas, Bracknell (GB); Renaud Perrin, Bracknell (GB); Stephen Christopher Smith, Bracknell (GB)

(73) Assignee: SYNGENTA PARTICIPATIONS AG, Basel (CH)

( * ) Notice: Subject to any disclaimer, the term of this patent is extended or adjusted under 35 U.S.C. 154(b) by 99 days.

(21) Appl. No.: 16/768,269

(22) PCT Filed: Nov. 26, 2018

(86) PCT No.: PCT/EP2018/082490
§ 371 (c)(1),
(2) Date: May 29, 2020

(87) PCT Pub. No.: WO2019/034796
PCT Pub. Date: Feb. 21, 2019

(65) Prior Publication Data
US 2020/0367498 A1  Nov. 26, 2020

(30) Foreign Application Priority Data

Dec. 1, 2017 (EP) .................................... 17205018

(51) Int. Cl.
*A01N 43/54* (2006.01)
*A01N 43/72* (2006.01)
*A01N 43/40* (2006.01)
*A01N 43/56* (2006.01)
*A01N 43/653* (2006.01)
*A01N 41/10* (2006.01)
*C07D 239/52* (2006.01)

(52) U.S. Cl.
CPC ............. *A01N 43/54* (2013.01); *A01N 41/10* (2013.01); *A01N 43/40* (2013.01); *A01N 43/56* (2013.01); *A01N 43/653* (2013.01); *A01N 43/72* (2013.01); *C07D 239/52* (2013.01)

(58) Field of Classification Search
CPC ........ A01N 43/54; A01N 43/40; A01N 43/56; A01N 43/653; A01N 43/72; A01N 41/10; C07D 239/52
See application file for complete search history.

(56) References Cited

U.S. PATENT DOCUMENTS

2006/0014960 A1   1/2006   Beckmann et al.

FOREIGN PATENT DOCUMENTS

WO     2003076415        9/2003
WO     WO-03076415 A1 *  9/2003 ............. A01N 43/54

OTHER PUBLICATIONS

Mariano et al. Environmentalchemistryletters, (2013), 12(1), p. 85-95 (see IDS).*
Mariano et al., Environmentalchemistryletters, (2013), 12(1), p. 85-95. (Disclosed in IDS and provided).*
International Search Report for International Application No. PCT/EP2018/082490 dated Jan. 25, 2019.
Extended European Search Report for EP Application No. 71205018.9 dated Mar. 6, 2018.
Castro Mariano J. et al., "Advances in Surfactants for Agrochemicals", Environmental Chemistry Letters, vol. 12(1), pp. 85-95, Jul. 6, 2013 (XP035343216).

* cited by examiner

*Primary Examiner* — Yong L Chu
(74) *Attorney, Agent, or Firm* — Bakerhostetler; Toni-Junell Herbert

(57) ABSTRACT

This invention relates to pyrimidine derivatives, to compositions comprising the pyrimidine derivatives, to methods of making and using these compositions, and to the use of the pyrimidine derivatives as adjuvants, particularly for agrochemical use. In particular, the present invention relates to compositions comprising the pyrimidine derivatives selected from emulsifiable concentrates (EC), emulsions in water (EW), suspensions of particles in water (SC), soluble liquids (SL), capsule suspensions (CS), suspensions of particles with an emulsion (SE), dispersion concentrates (DC), suspensions of particles in oil (OD), water dispersible granules (WG), soluble granules (SG) and wettable powders (WP).

13 Claims, No Drawings

PYRIMIDINE DERIVATIVES

CROSS-REFERENCE TO RELATED APPLICATIONS

This application is a 371 National Stage application of International Application No. PCT/EP2018/082490 filed Nov. 26, 2018 which claims priority to EP 17205018.9, filed Dec. 1, 2017, the entire contents of which applications are hereby incorporated by reference.

TECHNICAL FIELD

This invention relates to pyrimidine derivatives, to compositions comprising the pyrimidine derivatives, to methods of making and using these compositions, and to the use of the pyrimidine derivatives as adjuvants, particularly for agrochemical use. In particular, the present invention relates to compositions comprising the pyrimidine derivatives selected from emulsifiable concentrates (EC), emulsions in water (EW), suspensions of particles in water (SC), soluble liquids (SL), capsule suspensions (CS), suspensions of particles with an emulsion (SE), dispersion concentrates (DC), suspensions of particles in oil (OD), water dispersible granules (WG), soluble granules (SG) and wettable powders (WP).

BACKGROUND

The efficacy of a biologically active ingredient (AI), for example an agrochemical, in a composition can often be improved by the addition of further ingredients. The observed efficacy of the combination of ingredients can sometimes be significantly higher than that which would be expected from the individual ingredients used. An adjuvant is a substance which can increase the biological activity of an AI but is itself not significantly biologically active. The adjuvant is often a surfactant, and may be included in a formulation or added separately, and is often referred to as being built into formulations or added as tank mix additives.

In addition to the effect on biological activity, the physical properties of an adjuvant are of key importance and must be selected with a view to compatibility with the formulation concerned. For instance, it is generally simpler to incorporate a solid adjuvant into a solid formulation such as a water-soluble or water-dispersible granule. Some adjuvants rely on surfactant properties for biological activity enhancement and one typical class of adjuvants involves an alkyl or aryl group to provide a lipophilic moiety and a (poly)alkoxy chain to provide a hydrophilic moiety. Much has been published on the selection of adjuvants for various purposes, such as Hess, F. D. and Foy, C. L., Weed technology 2000, 14, 807-813. However, there is always a need for further novel adjuvants with novel properties.

DESCRIPTION OF THE INVENTION

The present invention is based on the finding that certain pyrimidine derivatives are surprisingly effective adjuvants, significantly enhancing the biological activity of active ingredients.

Thus, in a first aspect of the present invention, as embodiment 1, there is provided a compound of formula (I), or a salt thereof,

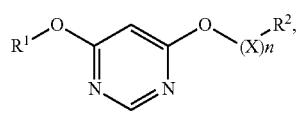

wherein
$R^1$ is selected from $C_4$-$C_{20}$-alkyl and $C_4$-$C_{20}$-alkenyl;
$R^2$ is selected from H, methyl, ethyl, n-propyl, isopropyl, n-butyl, isobutyl, s-butyl and t-butyl;
X is either

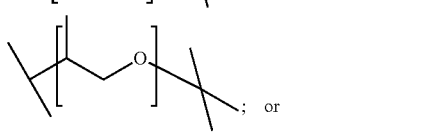

a mixture of

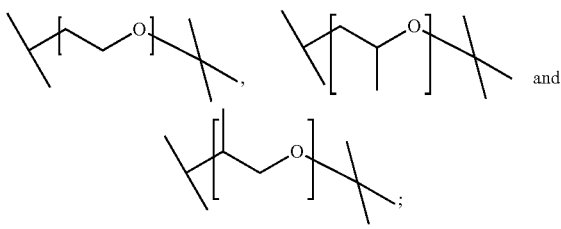

n is from 2 to 30.

As embodiment 2, there is provided a compound or salt according to embodiment 1, wherein
X is

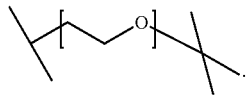

As embodiment 3, there is provided a compound or salt according to embodiment 1, wherein
X is

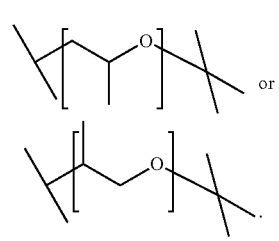

As embodiment 4, there is provided a compound according to embodiment 2, wherein n is from 5 to 15.

As embodiment 5, there is provided a compound according to embodiment 2, wherein n is from 7 to 12.

As embodiment 6, there is provided a compound according to embodiment 3, wherein n is from 2 to 15.

As embodiment 7, there is provided a compound according to embodiment 3, wherein n is from 2 to 8.

As embodiment 8, there is provided a compound according to embodiment 1, 2, 4 and 5, wherein $R^2$ is selected from H and methyl, in particular methyl.

As embodiment 9, there is provided a compound according to embodiment 1, 3, 6 and 7, wherein $R^2$ is selected from H and methyl, in particular methyl.

As embodiment 10, there is provided a compound according to any one of embodiments 1 to 9, wherein $R^1$ is selected from $C_6$-$C_{18}$-alkyl and $C_6$-$C_{18}$-alkenyl.

As embodiment 11, there is provided a compound according to embodiment 10, wherein $R^1$ is selected from hexyl, nonyl, dodecyl, hexadecyl, isostearyl and oleyl, in particular hexyl, nonyl, dodecyl, hexadecyl and oleyl, in particular hexyl, nonyl, dodecyl, hexadecyl and oleyl, more particularly oleyl.

As embodiment 12, there is provided a compound or salt of embodiment 1 of formula (I)

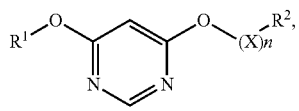

wherein
$R^1$ is selected from $C_6$-$C_{18}$-alkyl and $C_6$-$C_{18}$-alkenyl;
X is

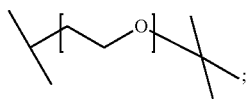

n is from 2 to 20;
$R^2$ is methyl or H.

As embodiment 12.1, there is provided a compound according to embodiment 1 of formula (I)

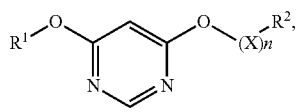

wherein
$R^1$ is selected from hexyl, nonyl, dodecyl, hexadecyl and oleyl;
X is

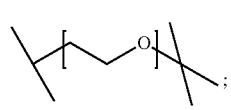

n is from 2 to 20;
$R^2$ is methyl or H.

As embodiment 13, there is provided a compound according to embodiment 12.1 wherein $R^2$ is methyl and $R^1$ and n are as defined in the table

| Compound | $R^1$ | n |
|---|---|---|
| 1 | Hexyl | 2 |
| 2 | Hexyl | 10 |
| 3 | Hexyl | 20 |
| 4 | Nonyl | 7 |
| 5 | Nonyl | 10 |
| 6 | Dodecyl | 7 |
| 7 | Dodecyl | 10 |
| 8 | Hexadecyl | 10 |
| 9 | Oleyl | 2 |
| 10 | Oleyl | 10 |
| 11 | Oleyl | 20 |

As embodiment 14, there is provided a compound according to embodiment 1 of formula (I)

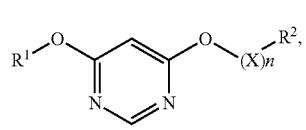

wherein
$R^1$ is selected from $C_6$-$C_{18}$-alkyl and $C_6$-$C_{18}$-alkenyl;
X is

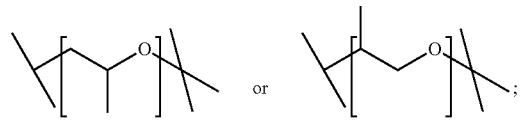

n is from 2 to 8;
$R^2$ is methyl or H.

As embodiment 14.1, there is provided a compound according to embodiment 1 of formula (I)

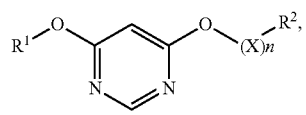

wherein
$R^1$ is selected from hexyl, nonyl, dodecyl, hexadecyl and oleyl;
X is

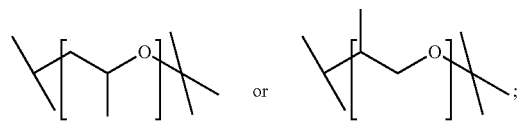

n is from 2 to 8;
$R^2$ is methyl or H.

As embodiment 15, there is provided a compound according to embodiment 14.1 wherein $R^1$ is dodecyl, $R^2$ is methyl and n is 3.

Definitions

The term "$C_4$-$C_{20}$-alkyl" as used herein—in isolation or as part of a chemical group—represents a straight-chain or branched hydrocarbon group having from 4 to 20 carbon atoms, for example n-butyl, isobutyl, sec-butyl, tert-butyl, pentyl, 1-methylbutyl, 2-methylbutyl, 3-methylbutyl, 1,2-dimethylpropyl, 1,1-dimethylpropyl, 2,2-dimethylpropyl, 1-ethylpropyl, hexyl, 1-methylpentyl, 2-methylpentyl, 3-methylpentyl, 4-methylpentyl, 1,2-dimethylpropyl, 1,3-dimethylbutyl, 1,4-dimethylbutyl, 2,3-dimethylbutyl, 1,1-dimethylbutyl, 2,2-dimethylbutyl, 3,3-dimethylbutyl, 1,1,2-trimethylpropyl, 1,2,2-trimethylpropyl, 1-ethylbutyl, 2-ethylbutyl.

The term "$C_4$-$C_{20}$-alkenyl" as used herein—in isolation or as part of a chemical group—represents a straight-chain or branched hydrocarbon group having from 4 to 20 carbon atoms and at least one double bond, for example 2-butenyl, 3-butenyl, 1-methyl-2-propenyl, 2-methyl-2-propenyl, 2-pentenyl, 3-pentenyl, 4-pentenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-2-propenyl, 1-ethyl-2-propenyl, 2-hexenyl, 3-hexenyl, 4-hexenyl, 5-hexenyl, 1-methyl-2-pentenyl, 2-methyl-2-pentenyl, 3-methyl-2-pentenyl, 4-methyl-2-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-2-butenyl, 1,2-dimethyl-3-butenyl, 1,3-dimethyl-2-butenyl, 2,2-dimethyl-3-butenyl, 2,3-dimethyl-2-butenyl, 2,3-dimethyl-3-butenyl, 1-ethyl-2-butenyl, 1-ethyl-3-butenyl, 2-ethyl-2-butenyl, 2-ethyl-3-butenyl, 1,1,2-trimethyl-2-propenyl, 1-ethyl-1-methyl-2-propenyl, 1-ethyl-2-methyl-2-propenyl, oleyl.

As used herein, when one embodiment refers to several other embodiments by using the term "according to any one of", for example "according to any one of embodiments 1 to 23", then said embodiment refers not only to embodiments indicated by integers such as 1 and 2 but also to embodiments indicated by numbers with a decimal component such as for example 23.1, 23.2, 23.3, 23.4, 23.20, 23.25, 23.30.

The compounds according to any one of embodiments 1 to 15 may be prepared as shown in Scheme 1.

Scheme 1

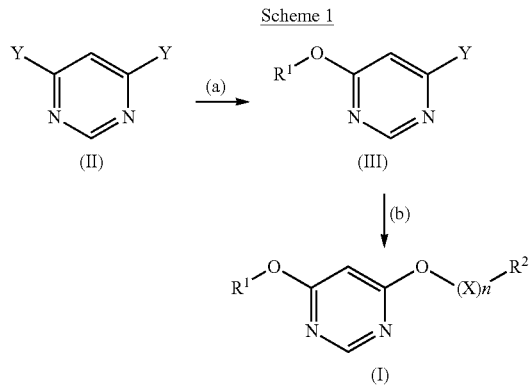

wherein $R^1$, $R^2$, X and n have the same meaning as in any one of embodiments 1 to 15, and Y is a suitable leaving group such as a halogen, for example fluoro or chloro.

Compounds of formula (II) are commercially available.

Step (a): Compounds of formula (III) may be prepared by reacting a compound of formula (II) with an alcohol $R^1$—OH wherein $R^1$ is defined as in any one of embodiments 1 to 15 in the presence of a suitable organolithium reagent such as lithium tert-butoxide, in a suitable solvent such as THF, under suitable conditions such as under inert gas (nitrogen) atmosphere and at a suitable temperature such as <5° C.

Step (b): Compounds of formula (III) are further reacted with a compound $R^2$—(O—$CH_2$—$CH_2$)$_n$—OH or $R^2$—(O—$CH_2(CH_3)$—$CH_2$)$_m$—OH wherein $R^2$ is defined as in any one of embodiments 1 to 15 in the presence of a suitable base such as potassium tert-butoxide, in a suitable solvent, for example DMSO, under suitable conditions such under inert gas (nitrogen) atmosphere and temperatures <5° C.

The present invention is based on the unexpected finding that compounds according to any one of embodiments 1 to 15 are particularly good adjuvants for biologically active ingredients, such as agrochemicals, pharmaceuticals and cosmetics and they may be especially effective in agrochemical formulations.

Hence, in a second aspect of the present invention, as embodiment 16, there is provided a composition comprising a biologically active ingredient, particularly an agrochemical active ingredient, and a compound according to any one of embodiments 1 to 15. In one embodiment 17, there is provided an agrochemical composition comprising (i) an active ingredient, (ii) a surfactant, and (iii) a compound according to any one of embodiments 1 to 15.

In a third aspect of the present invention, as embodiment 18 there is provided a tank-mix formulation comprising a compounds according to any one of embodiments 1 to 15.

In a fourth aspect, as embodiment 19, there is provided the use of an agrochemical composition as described in embodiments 16-17 to control pests.

In a fifth aspect, as embodiment 20, there is provided a method of controlling a pest, comprising applying a composition according to embodiment 16-17 to said pest or to the locus of said pest.

In a sixth aspect, as embodiment 21, there is provided a method of making an agrochemical composition according to embodiment 16-17, comprising combining a biologically active ingredient and compound according to any one of embodiments 1-15.

In a seventh aspect, as embodiment 22, there is provided the use of a compound according to any one of embodiments 1 to 15 as an adjuvant in a composition according to embodiments 16-17. The term "adjuvant" as used herein is a substance which can increase the biological activity of an AI but is itself not significantly biologically active.

Accordingly, the compounds according to any one of embodiments 1-15 may be combined with an active ingredient, which is suitably an agrochemical, in order to form a composition, suitably an agrochemical composition. The present invention extends to a method of making such a composition, wherein said method comprises combining a compound according to any one of embodiment 1-15 with a biologically active ingredient, and optionally a surfactant. The noun "agrochemical" and term "agrochemically active ingredient" are used herein interchangeably, and they include herbicides, insecticides, nematicides, molluscicides, fungicides, plant growth regulators and safeners; preferably herbicides, insecticides and fungicides.

The following combinations of the compounds according to any one of embodiments 1 to 15 with active ingredients are preferred (the abbreviation "TX" means "one compound selected from the compounds according to any one of embodiments 1 to 15):

an acaricide selected from the group of substances consisting of 1,1-bis(4-chlorophenyl)-2-ethoxyethanol (IUPAC name) (910)+TX, 2,4-dichlorophenyl benzenesulfonate (IUPAC/Chemical Abstracts name) (1059)+TX, 2-fluoro-N-methyl-N-1-naphthylacetamide (IUPAC name) (1295)+TX, 4-chlorophenyl phenyl sulfone (IUPAC name) (981)+TX, abamectin (1)+TX, acequinocyl (3)+TX, acetoprole [CCN]+TX, acrinathrin (9)+TX, aldicarb (16)+TX, aldoxycarb (863)+TX, alpha-cypermethrin (202)+TX, amidithion (870)+TX, amidoflumet [CCN]+TX, amidothioate (872)+TX, amiton (875)+TX, amiton hydrogen oxalate (875)+TX, amitraz (24)+TX, aramite (881)+TX, arsenous oxide (882)+TX, AVI 382 (compound code)+TX, AZ 60541 (compound code)+TX, azinphos-ethyl (44)+TX, azinphos-methyl (45)+TX, azobenzene (IUPAC name) (888)+TX, azocyclotin (46)+TX, azothoate (889)+TX, benomyl (62)+TX, benoxafos (alternative name) [CCN]+TX, benzoximate (71)+TX, benzyl benzoate (IUPAC name) [CCN]+TX, bifenazate (74)+TX, bifenthrin (76)+TX, binapacryl (907)+TX, brofenvalerate (alternative name)+TX, bromocyclen (918)+TX, bromophos (920)+TX, bromophos-ethyl (921)+TX, bromopropylate (94)+TX, buprofezin (99)+TX, butocarboxim (103)+TX, butoxycarboxim (104)+TX, butylpyridaben (alternative name)+TX, calcium polysulfide (IUPAC name) (111)+TX, camphechlor (941)+TX, carbanolate (943)+TX, carbaryl (115)+TX, carbofuran (118)+TX, carbophenothion (947)+TX, CGA 50'439 (development code) (125)+TX, chinomethionat (126)+TX, chlorbenside (959)+TX, chlordimeform (964)+TX, chlordimeform hydrochloride (964)+TX, chlorfenapyr (130)+TX, chlorfenethol (968)+TX, chlorfenson (970)+TX, chlorfensulfide (971)+TX, chlorfenvinphos (131)+TX, chlorobenzilate (975)+TX, chloromebuform (977)+TX, chloromethiuron (978)+TX, chloropropylate (983)+TX, chlorpyrifos (145)+TX, chlorpyrifos-methyl (146)+TX, chlorthiophos (994)+TX, cinerin I (696)+TX, cinerin II (696)+TX, cinerins (696)+TX, clofentezine (158)+TX, closantel (alternative name) [CCN]+TX, coumaphos (174)+TX, crotamiton (alternative name) [CCN]+TX, crotoxyphos (1010)+TX, cufraneb (1013)+TX, cyanthoate (1020)+TX, cyflumetofen (CAS Reg. No.: 400882-07-7)+TX, cyhalothrin (196)+TX, cyhexatin (199)+TX, cypermethrin (201)+TX, DCPM (1032)+TX, DDT (219)+TX, demephion (1037)+TX, demephion-O (1037)+TX, demephion-S (1037)+TX, demeton (1038)+TX, demeton-methyl (224)+TX, demeton-O (1038)+TX, demeton-O-methyl (224)+TX, demeton-S (1038)+TX, demeton-S-methyl (224)+TX, demeton-S-methylsulfon (1039)+TX, diafenthiuron (226)+TX, dialifos (1042)+TX, diazinon (227)+TX, dichlofluanid (230)+TX, dichlorvos (236)+TX, dicliphos (alternative name)+TX, dicofol (242)+TX, dicrotophos (243)+TX, dienochlor (1071)+TX, dimefox (1081)+TX, dimethoate (262)+TX, dinactin (alternative name) (653)+TX, dinex (1089)+TX, dinex-diclexine (1089)+TX, dinobuton (269)+TX, dinocap (270)+TX, dinocap-4 [CCN]+TX, dinocap-6 [CCN]+TX, dinocton (1090)+TX, dinopenton (1092)+TX, dinosulfon (1097)+TX, dinoterbon (1098)+TX, dioxathion (1102)+TX, diphenyl sulfone (IUPAC name) (1103)+TX, disulfiram (alternative name) [CCN]+TX, disulfoton (278)+TX, DNOC (282)+TX, dofenapyn (1113)+TX, doramectin (alternative name) [CCN]+TX, endosulfan (294)+TX, endothion (1121)+TX, EPN (297)+TX, eprinomectin (alternative name) [CCN]+TX, ethion (309)+TX, ethoate-methyl (1134)+TX, etoxazole (320)+TX, etrimfos (1142)+TX, fenazaflor (1147)+TX, fenazaquin (328)+TX, fenbutatin oxide (330)+TX, fenothiocarb (337)+TX, fenpropathrin (342)+TX, fenpyrad (alternative name)+TX, fenpyroximate (345)+TX, fenson (1157)+TX, fentrifanil (1161)+TX, fenvalerate (349)+TX, fipronil (354)+TX, fluacrypyrim (360)+TX, fluazuron (1166)+TX, flubenzimine (1167)+TX, flucycloxuron (366)+TX, flucythrinate (367)+TX, fluenetil (1169)+TX, flufenoxuron (370)+TX, flumethrin (372)+TX, fluorbenside (1174)+TX, fluvalinate (1184)+TX, FMC 1137 (development code) (1185)+TX, formetanate (405)+TX, formetanate hydrochloride (405)+TX, formothion (1192)+TX, formparanate (1193)+TX, gamma-HCH (430)+TX, glyodin (1205)+TX, halfenprox (424)+TX, heptenophos (432)+TX, hexadecyl cyclopropanecarboxylate (IUPAC/Chemical Abstracts name) (1216)+TX, hexythiazox (441)+TX, iodomethane (IUPAC name) (542)+TX, isocarbophos (alternative name) (473)+TX, isopropyl O-(methoxyaminothiophosphoryl)salicylate (IUPAC name) (473)+TX, ivermectin (alternative name) [CCN]+TX, jasmolin I (696)+TX, jasmolin II (696)+TX, jodfenphos (1248)+TX, lindane (430)+TX, lufenuron (490)+TX, malathion (492)+TX, malonoben (1254)+TX, mecarbam (502)+TX, mephosfolan (1261)+TX, mesulfen (alternative name) [CCN]+TX, methacrifos (1266)+TX, methamidophos (527)+TX, methidathion (529)+TX, methiocarb (530)+TX, methomyl (531)+TX, methyl bromide (537)+TX, metolcarb (550)+TX, mevinphos (556)+TX, mexacarbate (1290)+TX, milbemectin (557)+TX, milbemycin oxime (alternative name) [CCN]+TX, mipafox (1293)+TX, monocrotophos (561)+TX, morphothion (1300)+TX, moxidectin (alternative name) [CCN]+TX, naled (567)+TX, NC-184 (compound code)+TX, NC-512 (compound code)+TX, nifluridide (1309)+TX, nikkomycins (alternative name) [CCN]+TX, nitrilacarb (1313)+TX, nitrilacarb 1:1 zinc chloride complex (1313)+TX, NNI-0101 (compound code)+TX, NNI-0250 (compound code)+TX, omethoate (594)+TX, oxamyl (602)+TX, oxydeprofos (1324)+TX, oxydisulfoton (1325)+TX, pp'-DDT (219)+TX, parathion (615)+TX, permethrin (626)+TX, petroleum oils (alternative name) (628)+TX, phenkapton (1330)+TX, phenthoate (631)+TX, phorate (636)+TX, phosalone (637)+TX, phosfolan (1338)+TX, phosmet (638)+TX, phosphamidon (639)+TX, phoxim (642)+TX, pirimiphos-methyl (652)+TX, polychloroterpenes (traditional name) (1347)+TX, polynactins (alternative name) (653)+TX, proclonol (1350)+TX, profenofos (662)+TX, promacyl (1354)+TX, propargite (671)+TX, propetamphos (673)+TX, propoxur (678)+TX, prothidathion (1360)+TX, prothoate (1362)+TX, pyrethrin I (696)+TX, pyrethrin II (696)+TX, pyrethrins (696)+TX, pyridaben (699)+TX, pyridaphenthion (701)+TX, pyrimidifen (706)+TX, pyrimitate (1370)+TX, quinalphos (711)+TX, quintiofos (1381)+TX, R-1492 (development code) (1382)+TX, RA-17 (development code) (1383)+TX, rotenone (722)+TX, schradan (1389)+TX, sebufos (alternative name)+TX, selamectin (alternative name) [CCN]+TX, SI-0009 (compound code)+TX, sophamide (1402)+TX, spirodiclofen (738)+TX, spiromesifen (739)+TX, SSI-121 (development code) (1404)+TX, sulfiram (alternative name) [CCN]+TX, sulfluramid (750)+TX, sulfotep (753)+TX, sulfur (754)+TX, SZI-121 (development code) (757)+TX, tau-fluvalinate (398)+TX, tebufenpyrad (763)+TX, TEPP (1417)+TX, terbam (alternative name)+TX, tetrachlorvinphos (777)+TX, tetradifon (786)+TX, tetranactin (alternative name) (653)+TX, tetrasul (1425)+TX, thiafenox (alternative name)+TX, thiocarboxime (1431)+TX, thiofanox (800)+TX, thiometon (801)+TX, thioquinox (1436)+TX, thuringiensin (alternative name) [CCN]+TX, triamiphos (1441)+TX, triarathene (1443)+TX, triazophos (820)+TX, triazuron (alternative name)+TX, trichlorfon (824)+TX, trifenofos (1455)+TX, trinactin (alternative name) (653)+TX, vamidothion (847)+TX, vaniliprole [CCN] and YI-5302 (compound code)+TX, an algicide selected from the group of substances consisting of bethoxazin [CCN]+TX, copper dioctanoate (IUPAC name) (170)+TX, copper sulfate (172)+TX, cybutryne [CCN]+TX, dichlone (1052)+TX, dichlorophen (232)+TX, endothal (295)+TX, fentin (347)+TX, hydrated lime [CCN]+TX, nabam (566)+TX, quinoclamine (714)+TX, quinonamid (1379)+TX, simazine (730)+TX, triphenyltin acetate (IUPAC name) (347) and triphenyltin hydroxide (IUPAC name) (347)+TX, an anthelmintic selected from the group of substances consisting of abamectin (1)+TX, crufomate (1011)+TX, doramectin (alternative name) [CCN]+TX, emamectin (291)+TX, emamectin benzoate (291)+TX, eprinomectin (alternative name) [CCN]+TX, ivermectin (alternative name) [CCN]+TX, milbemycin oxime (alternative name) [CCN]+TX, moxidectin (alternative name) [CCN]+TX, piperazine [CCN]+TX, selamectin (alternative name) [CCN]+TX, spinosad (737) and thiophanate (1435)+TX, an avicide selected from the group of substances consisting of chloralose (127)+TX, endrin (1122)+TX, fenthion (346)+TX, pyridin-4-amine (IUPAC name) (23) and strychnine (745)+TX, a bactericide selected from the group of substances consisting of 1-hydroxy-1H-pyridine-2-thione (IUPAC name) (1222)+TX, 4-(quinoxalin-2-ylamino)benzenesulfonamide (IUPAC name) (748)+TX, 8-hydroxyquinoline sulfate (446)+TX, bronopol (97)+TX, copper dioctanoate (IUPAC name) (170)+TX, copper hydroxide (IUPAC name) (169)+TX, cresol [CCN]+TX, dichlorophen (232)+TX, dipyrithione (1105)+TX, dodicin (1112)+TX, fenaminosulf (1144)+TX, formaldehyde (404)+TX, hydrargaphen (alternative name) [CCN]+TX, kasugamycin (483)+TX, kasugamycin hydrochloride hydrate (483)+TX, nickel bis(dimethyldithiocarbamate) (IUPAC name) (1308)+TX, nitrapyrin (580)+TX, octhilinone (590)+TX, oxolinic acid (606)+TX, oxytetracycline (611)+TX, potassium hydroxyquinoline sulfate (446)+TX, probenazole (658)+TX, streptomycin (744)+TX, streptomycin sesquisulfate (744)+TX, tecloftalam (766)+TX, and thiomersal (alternative name) [CCN]+TX, a biological agent selected from the group of substances consisting of *Adoxophyes orana* GV (alternative name) (12)+TX, *Agrobacterium radiobacter* (alternative name) (13)+TX, *Amblyseius* spp. (alternative name) (19)+TX, *Anagrapha falcifera* NPV (alternative name) (28)+TX, *Anagrus atomus* (alternative name) (29)+TX, *Aphelinus abdominalis* (alternative name) (33)+TX, *Aphidius colemani* (alternative name) (34)+TX, *Aphidoletes aphidimyza* (alternative name) (35)+TX, *Autographa californica* NPV (alternative name) (38)+TX, *Bacillus firmus* (alternative name) (48)+TX, *Bacillus sphaericus* Neide (scientific name) (49)+TX, *Bacillus thuringiensis* Berliner (scientific name) (51)+TX, *Bacillus thuringiensis* subsp. *aizawai* (scientific name) (51)+TX, *Bacillus thuringiensis* subsp. *israelensis* (scientific name) (51)+TX, *Bacillus thuringiensis* subsp. *japonensis* (scientific name) (51)+TX, *Bacillus thuringiensis* subsp. *kurstaki* (scientific name) (51)+TX, *Bacillus thuringiensis* subsp. *tenebrionis* (scientific name) (51)+TX, *Beauveria bassiana* (alternative name) (53)+TX, *Beauveria brongniartii* (alternative name) (54)+TX, *Chrysoperla carnea* (alternative name) (151)+TX, *Cryptolaemus montrouzieri* (alternative name) (178)+TX, *Cydia pomonella* GV (alternative name) (191)+TX, *Dacnusa sibirica* (alternative name) (212)+TX, *Diglyphus isaea* (alternative name) (254)+TX, *Encarsia formosa* (scientific name) (293)+TX, *Eretmocerus eremicus* (alternative name) (300)+TX, *Helicoverpa zea* NPV (alternative name) (431)+TX, *Heterorhabditis bacteriophora* and *H. megidis* (alternative name) (433)+TX, *Hippodamia convergens* (alternative name) (442)+TX, *Leptomastix dactylopii* (alternative name) (488)+TX, *Macrolophus caliginosus* (alternative name) (491)+TX, *Mamestra brassicae* NPV (alternative name) (494)+TX, *Metaphycus helvolus* (alternative name) (522)+TX, *Metarhizium anisopliae* var. *acridum* (scientific name) (523)+TX, *Metarhizium anisopliae* var. *anisopliae* (scientific name) (523)+TX, *Neodiprion sertifer* NPV and *N. lecontei* NPV (alternative name) (575)+TX, *Orius* spp. (alternative name) (596)+TX, *Paecilomyces fumosoroseus* (alternative name) (613)+TX, *Phytoseiulus persimilis* (alternative name) (644)+TX, *Spodoptera exigua* multicapsid nuclear polyhedrosis virus (scientific name) (741)+TX, *Steinernema bibionis* (alternative name) (742)+TX, *Steinernema carpocapsae* (alternative name) (742)+TX, *Steinernema feltiae* (alternative name) (742)+TX, *Steinernema glaseri* (alternative name) (742)+TX, *Steinernema riobrave* (alternative name) (742)+TX, *Steinernema riobravis* (alternative name) (742)+TX, *Steinernema scapterisci* (alternative name) (742)+TX, *Steinernema* spp. (alternative name) (742)+TX, *Trichogramma* spp. (alternative name) (826)+TX, *Typhlodromus occidentalis* (alternative name) (844) and *Verticillium lecanii* (alternative name) (848)+TX, a soil sterilant selected from the group of substances consisting of iodomethane (IUPAC name) (542) and methyl bromide (537)+TX, a chemosterilant selected from the group of substances consisting of apholate [CCN]+TX, bisazir (alternative name) [CCN]+TX, busulfan (alternative name) [CCN]+TX, diflubenzuron (250)+TX, dimatif (alternative name) [CCN]+TX, hemel [CCN]+TX, hempa [CCN]+TX, metepa [CCN]+TX, methiotepa [CCN]+TX, methyl apholate [CCN]+TX, morzid [CCN]+TX, penfluron (alternative name) [CCN]+TX, tepa [CCN]+TX, thiohempa (alternative name) [CCN]+TX, thiotepa (alternative name) [CCN]+TX, tretamine (alternative name) [CCN] and uredepa (alternative name) [CCN]+TX, an insect pheromone selected from the group of substances consisting of (E)-dec-5-en-1-yl acetate with (E)-dec-5-en-1-ol (IUPAC name) (222)+TX, (E)-tridec-4-en-1-yl acetate (IUPAC name) (829)+TX, (E)-6-methylhept-2-en-4-ol (IUPAC name) (541)+TX, (E,Z)-tetradeca-4,10-dien-1-yl acetate (IUPAC name) (779)+TX, (Z)-dodec-7-en-1-yl acetate (IUPAC name) (285)+TX, (Z)-hexadec-11-enal (IUPAC name) (436)+TX, (Z)-hexadec-11-en-1-yl acetate (IUPAC name) (437)+TX, (Z)-hexadec-13-en-11-yn-1-yl acetate (IUPAC name) (438)+TX, (Z)-icos-13-en-10-one (IUPAC name) (448)+TX, (Z)-tetradec-7-en-1-al (IUPAC name) (782)+TX, (Z)-tetradec-9-en-1-ol (IUPAC name) (783)+TX, (Z)-tetradec-9-en-1-yl acetate (IUPAC name) (784)+TX, (7E,9Z)-dodeca-7,9-dien-1-ylacetate (IUPAC name) (283)+TX, (9Z,11E)-tetradeca-9,11-dien-1-yl acetate (IUPAC name) (780)+TX, (9Z,12E)-tetradeca-9,12-dien-1-yl acetate (IUPAC name) (781)+TX, 14-methyloctadec-1-ene (IUPAC name) (545)+TX, 4-methylnonan-5-ol with 4-methylnonan-5-one (IUPAC name) (544)+TX, alpha-multistriatin (alternative name) [CCN]+TX, brevicomin (alternative name) [CCN]+TX, codlelure (alternative name) [CCN]+TX, codlemone (alternative name) (167)+TX, cuelure (alternative name) (179)+TX, disparlure (277)+TX, dodec-8-en-1-yl acetate (IUPAC name) (286)+TX, dodec-9-en-1-yl acetate (IUPAC name) (287)+TX, dodeca-8+TX, 10-dien-1-yl acetate (IUPAC name) (284)+TX, dominicalure (alternative name) [CCN]+TX, ethyl 4-methyloctanoate (IUPAC name) (317)+TX, eugenol (alternative name) [CCN]+TX, frontalin (alternative name) [CCN]+TX, gossyplure (alternative name) (420)+TX, grandlure (421)+TX, grandlure I (alternative name) (421)+TX, grandlure II (alternative name) (421)+TX, grandlure III (alternative name) (421)+TX, grandlure IV (alternative name) (421)+TX, hexalure [CCN]+TX, ipsdienol (alternative name) [CCN]+TX, ipsenol (alternative name) [CCN]+TX, japonilure (alternative name) (481)+TX, lineatin (alternative name) [CCN]+TX, litlure (alternative name) [CCN]+TX, looplure (alternative name) [CCN]+TX, medlure [CCN]+TX, megatomoic acid (alternative name) [CCN]+TX, methyl eugenol (alternative name) (540)+TX, muscalure (563)+TX, octadeca-2,13-dien-1-yl acetate (IUPAC name) (588)+TX, octadeca-3,13-dien-1-yl acetate (IUPAC name) (589)+TX, orfralure (alternative name) [CCN]+TX, oryctalure (alternative name) (317)+TX, ostramone (alternative name) [CCN]+TX, siglure [CCN]+TX, sordidin (alternative name) (736)+TX, sulcatol (alternative name) [CCN]+TX, tetradec-11-en-1-yl acetate (IUPAC name) (785)+TX, trimedlure (839)+TX, trimedlure A (alternative name) (839)+TX, trimedlure $B_1$ (alternative name) (839)+TX, trimedlure $B_2$ (alternative name) (839)+TX, trimedlure C (alternative name) (839) and trunc-call (alternative name) [CCN]+TX, an insect repellent selected from the group of substances consisting of 2-(octylthio)ethanol (IUPAC name) (591)+TX, butopyronoxyl (933)+TX, butoxy(polypropylene glycol) (936)+TX, dibutyl adipate (IUPAC name) (1046)+TX, dibutyl phthalate (1047)+TX, dibutyl succinate (IUPAC name) (1048)+TX, diethyltoluamide [CCN]+TX, dimethyl carbate [CCN]+TX, dimethyl phthalate [CCN]+TX, ethyl hexanediol (1137)+TX, hexamide [CCN]+TX, methoquinbutyl (1276)+TX, methylneodecanamide [CCN]+TX, oxamate [CCN] and picaridin [CCN]+TX, an insecticide selected from the group of substances consisting of 1-dichloro-1-nitroethane (IUPAC/Chemical Abstracts name) (1058)+TX, 1,1-dichloro-2,2-bis(4-ethylphenyl)ethane (IUPAC name) (1056), +TX, 1,2-dichloropropane (IUPAC/Chemical Abstracts name) (1062)+TX, 1,2-dichloropropane with 1,3-dichloropropene (IUPAC name) (1063)+TX, 1-bromo-2-chloroethane (IUPAC/Chemical Abstracts name) (916)+TX, 2,2,2-trichloro-1-(3,4-dichlorophenyl)ethyl acetate (IUPAC name) (1451)+TX, 2,2-dichlorovinyl 2-ethylsulfinylethyl methyl phosphate (IUPAC name) (1066)+TX, 2-(1,3-dithiolan-2-yl)phenyl dimethylcarbamate (IUPAC/Chemical Abstracts name) (1109)+TX, 2-(2-butoxyethoxy)ethyl thiocyanate (IUPAC/Chemical Abstracts name) (935)+TX, 2-(4,5-dimethyl-1,3-dioxolan-2-yl)phenyl methylcarbamate (IUPAC/Chemical Abstracts name) (1084)+TX, 2-(4-chloro-3,5-xylyloxy) ethanol (IUPAC name) (986)+TX, 2-chlorovinyl diethyl phosphate (IUPAC name) (984)+TX, 2-imidazolidone (IUPAC name) (1225)+TX, 2-isovalerylindan-1,3-dione (IUPAC name) (1246)+TX, 2-methyl(prop-2-ynyl)aminophenyl methylcarbamate (IUPAC name) (1284)+TX, 2-thiocyanatoethyl laurate (IUPAC name) (1433)+TX, 3-bromo-1-chloroprop-1-ene (IUPAC name) (917)+TX, 3-methyl-1-phenylpyrazol-5-yl dimethylcarbamate (IUPAC name) (1283)+TX, 4-methyl(prop-2-ynyl)amino-3,5-xylyl methylcarbamate (IUPAC name) (1285)+TX, 5,5-dimethyl-3-oxocyclohex-1-enyl dimethylcarbamate (IUPAC name) (1085)+TX, abamectin (1)+TX, acephate (2)+TX, acetamiprid (4)+TX, acethion (alternative name) [CCN]+TX, acetoprole [CCN]+TX, acrinathrin (9)+TX, acrylonitrile (IUPAC name) (861)+TX, alanycarb (15)+TX, aldicarb (16)+TX, aldoxycarb (863)+TX, aldrin (864)+TX, allethrin (17)+TX, allosamidin (alternative name) [CCN]+TX, allyxycarb (866)+TX, alpha-cypermethrin (202)+TX, alpha-ecdysone (alternative name) [CCN]+TX, aluminium phosphide (640)+TX, amidithion (870)+TX, amidothioate (872)+TX, aminocarb (873)+TX, amiton (875)+TX, amiton hydrogen oxalate (875)+TX, amitraz (24)+TX, anabasine (877)+TX, athidathion (883)+TX, AVI 382 (compound code)+TX, AZ 60541 (compound code)+TX, azadirachtin (alternative name) (41)+TX, azamethiphos (42)+TX, azinphos-ethyl (44)+TX, azinphos-methyl (45)+TX, azothoate (889)+TX, *Bacillus thuringiensis* delta endotoxins (alternative name) (52)+TX, barium hexafluorosilicate (alternative name) [CCN]+TX, barium polysulfide (IUPAC/Chemical Abstracts name) (892)+TX, barthrin [CCN]+TX, Bayer 22/190 (development code) (893)+TX, Bayer 22408 (development code) (894)+TX, bendiocarb (58)+TX, benfuracarb (60)+TX, bensultap (66)+TX, beta-cyfluthrin (194)+TX, beta-cypermethrin (203)+TX, bifenthrin (76)+TX, bioallethrin (78)+TX, bioallethrin S-cyclopentenyl isomer (alternative name) (79)+TX, bioethanomethrin [CCN]+TX, biopermethrin (908)+TX, bioresmethrin (80)+TX, bis(2-chloroethyl) ether (IUPAC name) (909)+TX, bistrifluron (83)+TX, borax (86)+TX, brofenvalerate (alternative name)+TX, bromfenvinfos (914)+TX, bromocyclen (918)+TX, bromo-DDT (alternative name) [CCN]+TX, bromophos (920)+TX, bromophos-ethyl (921)+TX, bufencarb (924)+TX, buprofezin (99)+TX, butacarb (926)+TX, butathiofos (927)+TX, butocarboxim (103)+TX, butonate (932)+TX, butoxycarboxim (104)+TX, butylpyridaben (alternative name)+TX, cadusafos (109)+TX, calcium arsenate [CCN]+TX, calcium cyanide (444)+TX, calcium polysulfide (IUPAC name) (111)+TX, camphechlor (941)+TX, carbanolate (943)+TX, carbaryl (115)+TX, carbofuran (118)+TX, carbon disulfide (IUPAC/Chemical Abstracts name) (945)+TX, carbon tetrachloride (IUPAC name) (946)+TX, carbophenothion (947)+TX, carbosulfan (119)+TX, cartap (123)+TX, cartap hydrochloride (123)+TX, cevadine (alternative name) (725)+TX, chlorbicyclen (960)+TX, chlordane (128)+TX, chlordecone (963)+TX, chlordimeform (964)+TX, chlordimeform hydrochloride (964)+TX, chlorethoxyfos (129)+TX, chlorfenapyr (130)+TX, chlorfenvinphos (131)+TX, chlorfluazuron (132)+TX, chlormephos (136)+TX, chloroform [CCN]+TX, chloropicrin (141)+TX, chlorphoxim (989)+TX, chlorprazophos (990)+TX, chlorpyrifos (145)+TX, chlorpyrifos-methyl (146)+TX, chlorthiophos (994)+TX, chromafenozide (150)+TX, cinerin I (696)+TX, cinerin II (696)+TX, cinerins (696)+TX, cis-resmethrin (alternative name)+TX, cismethrin (80)+TX, clocythrin (alternative name)+TX, cloethocarb (999)+TX, closantel (alternative name) [CCN]+TX, clothianidin (165)+TX, copper acetoarsenite [CCN]+TX, copper arsenate [CCN]+TX, copper oleate [CCN]+TX, coumaphos (174)+TX, coumithoate (1006)+TX, crotamiton (alternative name) [CCN]+TX, crotoxyphos (1010)+TX, crufomate (1011)+TX, cryolite (alternative name) (177)+TX, CS 708 (development code) (1012)+TX, cyanofenphos (1019)+TX, cyanophos (184)+TX, cyanthoate (1020)+TX, cyclethrin [CCN]+TX, cycloprothrin (188)+TX, cyfluthrin (193)+TX, cyhalothrin (196)+TX, cypermethrin (201)+TX, cyphenothrin (206)+TX, cyromazine (209)+TX, cythioate (alternative name) [CCN]+TX, d-limonene (alternative name) [CCN]+TX, d-tetramethrin (alternative name) (788)+TX, DAEP (1031)+TX, dazomet (216)+TX, DDT (219)+TX, decarbofuran (1034)+TX, deltamethrin (223)+TX, demephion (1037)+TX, demephion-O (1037)+TX, demephion-S (1037)+TX, demeton (1038)+TX, demeton-methyl (224)+TX, demeton-O (1038)+TX, demeton-O-methyl (224)+TX, demeton-S (1038)+TX, demeton-S-methyl (224)+TX, demeton-S- methylsulphon (1039)+TX, diafenthiuron (226)+TX, dialifos (1042)+TX, diamidafos (1044)+TX, diazinon (227)+TX, dicapthon (1050)+TX, dichlofenthion (1051)+TX, dichlorvos (236)+TX, dicliphos (alternative name)+TX, dicresyl (alternative name) [CCN]+TX, dicrotophos (243)+TX, dicyclanil (244)+TX, dieldrin (1070)+TX, diethyl 5-methylpyrazol-3-yl phosphate (IUPAC name) (1076)+TX, diflubenzuron (250)+TX, dilor (alternative name) [CCN]+TX, dimefluthrin [CCN]+TX, dimefox (1081)+TX, dimetan (1085)+TX, dimethoate (262)+TX, dimethrin (1083)+TX, dimethylvinphos (265)+TX, dimetilan (1086)+TX, dinex (1089)+TX, dinex-diclexine (1089)+TX, dinoprop (1093)+TX, dinosam (1094)+TX, dinoseb (1095)+TX, dinotefuran (271)+TX, diofenolan (1099)+TX, dioxabenzofos (1100)+TX, dioxacarb (1101)+TX, dioxathion (1102)+TX, disulfoton (278)+TX, dithicrofos (1108)+TX, DNOC (282)+TX, doramectin (alternative name) [CCN]+TX, DSP (1115)+TX, ecdysterone (alternative name) [CCN]+TX, EI 1642 (development code) (1118)+TX, emamectin (291)+TX, emamectin benzoate (291)+TX, EMPC (1120)+TX, empenthrin (292)+TX, endosulfan (294)+TX, endothion (1121)+TX, endrin (1122)+TX, EPBP (1123)+TX, EPN (297)+TX, epofenonane (1124)+TX, eprinomectin (alternative name) [CCN]+TX, esfenvalerate (302)+TX, etaphos (alternative name) [CCN]+TX, ethiofencarb (308)+TX, ethion (309)+TX, ethiprole (310)+TX, ethoate-methyl (1134)+TX, ethoprophos (312)+TX, ethyl formate (IUPAC name) [CCN]+TX, ethyl-DDD (alternative name) (1056)+TX, ethylene dibromide (316)+TX, ethylene dichloride (chemical name) (1136)+TX, ethylene oxide [CCN]+TX, etofenprox (319)+TX, etrimfos (1142)+TX, EXD (1143)+TX, famphur (323)+TX, fenamiphos (326)+TX, fenazaflor (1147)+TX, fenchlorphos (1148)+TX, fenethacarb (1149)+TX, fenfluthrin (1150)+TX, fenitrothion (335)+TX, fenobucarb (336)+TX, fenoxacrim (1153)+TX, fenoxycarb (340)+TX, fenpirithrin (1155)+TX, fenpropathrin (342)+TX, fenpyrad (alternative name)+TX, fensulfothion (1158)+TX, fenthion (346)+TX, fenthion-ethyl [CCN]+TX, fenvalerate (349)+TX, fipronil (354)+TX, flonicamid (358)+TX, flubendiamide (CAS. Reg. No.: 272451-65-7)+TX, flucofuron (1168)+TX, flucycloxuron (366)+TX, flucythrinate (367)+TX, fluenetil (1169)+TX, flufenerim [CCN]+TX, flufenoxuron (370)+TX, flufenprox (1171)+TX, flumethrin (372)+TX, fluvalinate (1184)+TX, FMC 1137 (development code) (1185)+TX, fonofos (1191)+TX, formetanate (405)+TX, formetanate hydrochloride (405)+TX, formothion (1192)+TX, formparanate (1193)+TX, fosmethilan (1194)+TX, fospirate (1195)+TX, fosthiazate (408)+TX, fosthietan (1196)+TX, furathiocarb (412)+TX, furethrin (1200)+TX, gamma-cyhalothrin (197)+TX, gamma-HCH (430)+TX, guazatine (422)+TX, guazatine acetates (422)+TX, GY-81 (development code) (423)+TX, halfenprox (424)+TX, halofenozide (425)+TX, HCH (430)+TX, HEOD (1070)+TX, heptachlor (1211)+TX, heptenophos (432)+TX, heterophos [CCN]+TX, hexaflumuron (439)+TX, HHDN (864)+TX, hydramethylnon (443)+TX, hydrogen cyanide (444)+TX, hydroprene (445)+TX, hyquincarb (1223)+TX, imidacloprid (458)+TX, imiprothrin (460)+TX, indoxacarb (465)+TX, iodomethane (IUPAC name) (542)+TX, IPSP (1229)+TX, isazofos (1231)+TX, isobenzan (1232)+TX, isocarbophos (alternative name) (473)+TX, isodrin (1235)+TX, isofenphos (1236)+TX, isolane (1237)+TX, isoprocarb (472)+TX, isopropyl O-(methoxyaminothiophosphoryl)salicylate (IUPAC name) (473)+TX, isoprothiolane (474)+TX, isothioate (1244)+TX, isoxathion (480)+TX, ivermectin (alternative name) [CCN]+TX, jasmolin I (696)+TX, jasmolin II (696)+TX, jodfenphos (1248)+TX, juvenile hormone I (alternative name) [CCN]+TX, juvenile hormone II (alternative name) [CCN]+TX, juvenile hormone III (alternative name) [CCN]+TX, kelevan (1249)+TX, kinoprene (484)+TX, lambda-cyhalothrin (198)+TX, lead arsenate [CCN]+TX, lepimectin (CCN)+TX, leptophos (1250)+TX, lindane (430)+TX, lirimfos (1251)+TX, lufenuron (490)+TX, lythidathion (1253)+TX, m-cumenyl methylcarbamate (IUPAC name) (1014)+TX, magnesium phosphide (IUPAC name) (640)+TX, malathion (492)+TX, malonoben (1254)+TX, mazidox (1255)+TX, mecarbam (502)+TX, mecarphon (1258)+TX, menazon (1260)+TX, mephosfolan (1261)+TX, mercurous chloride (513)+TX, mesulfenfos (1263)+TX, metaflumizone (CCN)+TX, metam (519)+TX, metam-potassium (alternative name) (519)+TX, metam-sodium (519)+TX, methacrifos (1266)+TX, methamidophos (527)+TX, methanesulfonyl fluoride (IUPAC/Chemical Abstracts name) (1268)+TX, methidathion (529)+TX, methiocarb (530)+TX, methocrotophos (1273)+TX, methomyl (531)+TX, methoprene (532)+TX, methoquin-butyl (1276)+TX, methothrin (alternative name) (533)+TX, methoxychlor (534)+TX, methoxyfenozide (535)+TX, methyl bromide (537)+TX, methyl isothiocyanate (543)+TX, methylchloroform (alternative name) [CCN]+TX, methylene chloride [CCN]+TX, metofluthrin [CCN]+TX, metolcarb (550)+TX, metoxadiazone (1288)+TX, mevinphos (556)+TX, mexacarbate (1290)+TX, milbemectin (557)+TX, milbemycin oxime (alternative name) [CCN]+TX, mipafox (1293)+TX, mirex (1294)+TX, monocrotophos (561)+TX, morphothion (1300)+TX, moxidectin (alternative name) [CCN]+TX, naftalofos (alternative name) [CCN]+TX, naled (567)+TX, naphthalene (IUPAC/Chemical Abstracts name) (1303)+TX, NC-170 (development code) (1306)+TX, NC-184 (compound code)+TX, nicotine (578)+TX, nicotine sulfate (578)+TX, nifluridide (1309)+TX, nitenpyram (579)+TX, nithiazine (1311)+TX, nitrilacarb (1313)+TX, nitrilacarb 1:1 zinc chloride complex (1313)+TX, NNI-0101 (compound code)+TX, NNI-0250 (compound code)+TX, nornicotine (traditional name) (1319)+TX, novaluron (585)+TX, noviflumuron (586)+TX, O-5-dichloro-4-iodophenyl O-ethyl ethylphosphonothioate (IUPAC name) (1057)+TX, O,O-diethyl O-4-methyl-2-oxo-2H-chromen-7-yl phosphorothioate (IUPAC name) (1074)+TX, O,O-diethyl O-6-methyl-2-propylpyrimidin-4-yl phosphorothioate (IUPAC name) (1075)+TX, O,O,O'O,O'-tetrapropyl dithiopyrophosphate (IUPAC name) (1424)+TX, oleic acid (IUPAC name) (593)+TX, omethoate (594)+TX, oxamyl (602)+TX, oxydemetonmethyl (609)+TX, oxydeprofos (1324)+TX, oxydisulfoton (1325)+TX, pp'-DDT (219)+TX, para-dichlorobenzene [CCN]+TX, parathion (615)+TX, parathion-methyl (616)+TX, penfluron (alternative name) [CCN]+TX, pentachlorophenol (623)+TX, pentachlorophenyl laurate (IUPAC name) (623)+TX, permethrin (626)+TX, petroleum oils (alternative name) (628)+TX, PH 60-38 (development code) (1328)+TX, phenkapton (1330)+TX, phenothrin (630)+TX, phenthoate (631)+TX, phorate (636)+TX, phosalone (637)+TX, phosfolan (1338)+TX, phosmet (638)+TX, phosnichlor (1339)+TX, phosphamidon (639)+TX, phosphine (IUPAC name) (640)+TX, phoxim (642)+TX, phoxim-methyl (1340)+TX, pirimetaphos (1344)+TX, pirimicarb (651)+TX, pirimiphos-ethyl (1345)+TX, pirimiphos-methyl (652)+TX, polychlorodicyclopentadiene isomers (IUPAC name) (1346)+TX, polychloroterpenes (traditional name) (1347)+TX, potassium arsenite [CCN]+TX, potassium thiocyanate [CCN]+TX, prallethrin (655)+TX, precocene I (alternative name) [CCN]+TX, precocene II (alternative name) [CCN]+TX, precocene III (alternative name) [CCN]+TX, primidophos (1349)+TX, profenofos (662)+TX, profluthrin

[CCN]+TX, promacyl (1354)+TX, promecarb (1355)+TX, propaphos (1356)+TX, propetamphos (673)+TX, propoxur (678)+TX, prothidathion (1360)+TX, prothiofos (686)+TX, prothoate (1362)+TX, protrifenbute [CCN]+TX, pymetrozine (688)+TX, pyraclofos (689)+TX, pyrazophos (693)+TX, pyresmethrin (1367)+TX, pyrethrin I (696)+TX, pyrethrin II (696)+TX, pyrethrins (696)+TX, pyridaben (699)+TX, pyridalyl (700)+TX, pyridaphenthion (701)+TX, pyrimidifen (706)+TX, pyrimitate (1370)+TX, pyriproxyfen (708)+TX, quassia (alternative name) [CCN]+TX, quinalphos (711)+TX, quinalphos-methyl (1376)+TX, quinothion (1380)+TX, quintiofos (1381)+TX, R-1492 (development code) (1382)+TX, rafoxanide (alternative name) [CCN]+TX, resmethrin (719)+TX, rotenone (722)+TX, RU 15525 (development code) (723)+TX, RU 25475 (development code) (1386)+TX, ryania (alternative name) (1387)+TX, ryanodine (traditional name) (1387)+TX, sabadilla (alternative name) (725)+TX, schradan (1389)+TX, sebufos (alternative name)+TX, selamectin (alternative name) [CCN]+TX, SI-0009 (compound code)+TX, SI-0205 (compound code)+TX, SI-0404 (compound code)+TX, SI-0405 (compound code)+TX, silafluofen (728)+TX, SN 72129 (development code) (1397)+TX, sodium arsenite [CCN]+TX, sodium cyanide (444)+TX, sodium fluoride (IUPAC/Chemical Abstracts name) (1399)+TX, sodium hexafluorosilicate (1400)+TX, sodium pentachlorophenoxide (623)+TX, sodium selenate (IUPAC name) (1401)+TX, sodium thiocyanate [CCN]+TX, sophamide (1402)+TX, spinosad (737)+TX, spiromesifen (739)+TX, spirotetrmat (CCN)+TX, sulcofuron (746)+TX, sulcofuron-sodium (746)+TX, sulfluramid (750)+TX, sulfotep (753)+TX, sulfuryl fluoride (756)+TX, sulprofos (1408)+TX, tar oils (alternative name) (758)+TX, tau-fluvalinate (398)+TX, tazimcarb (1412)+TX, TDE (1414)+TX, tebufenozide (762)+TX, tebufenpyrad (763)+TX, tebupirimfos (764)+TX, teflubenzuron (768)+TX, tefluthrin (769)+TX, temephos (770)+TX, TEPP (1417)+TX, terallethrin (1418)+TX, terbam (alternative name)+TX, terbufos (773)+TX, tetrachloroethane [CCN]+TX, tetrachlorvinphos (777)+TX, tetramethrin (787)+TX, theta-cypermethrin (204)+TX, thiacloprid (791)+TX, thiafenox (alternative name)+TX, thiamethoxam (792)+TX, thicrofos (1428)+TX, thiocarboxime (1431)+TX, thiocyclam (798)+TX, thiocyclam hydrogen oxalate (798)+TX, thiodicarb (799)+TX, thiofanox (800)+TX, thiometon (801)+TX, thionazin (1434)+TX, thiosultap (803)+TX, thiosultap-sodium (803)+TX, thuringiensin (alternative name) [CCN]+TX, tolfenpyrad (809)+TX, tralomethrin (812)+TX, transfluthrin (813)+TX, transpermethrin (1440)+TX, triamiphos (1441)+TX, triazamate (818)+TX, triazophos (820)+TX, triazuron (alternative name)+TX, trichlorfon (824)+TX, trichlormetaphos-3 (alternative name) [CCN]+TX, trichloronat (1452)+TX, trifenofos (1455)+TX, triflumuron (835)+TX, trimethacarb (840)+TX, triprene (1459)+TX, vamidothion (847)+TX, vaniliprole [CCN]+TX, veratridine (alternative name) (725)+TX, veratrine (alternative name) (725)+TX, XMC (853)+TX, xylylcarb (854)+TX, YI-5302 (compound code)+TX, zeta-cypermethrin (205)+TX, zetamethrin (alternative name)+TX, zinc phosphide (640)+TX, zolaprofos (1469) and ZXI 8901 (development code) (858)+TX, cyantraniliprole [736994-63-19+TX, chlorantraniliprole [500008-45-7]+TX, cyenopyrafen [560121-52-0]+TX, cyflumetofen [400882-07-7]+TX, pyrifluquinazon [337458-27-2]+TX, spinetoram [187166-40-1+187166-15-0]+TX, spirotetramat [203313-25-1]+TX, sulfoxaflor [946578-00-3]+TX, flufiprole [704886-18-0]+TX, meperfluthrin [915288-13-0]+TX, tetramethylfluthrin [84937-88-2]+TX, triflumezopyrim (disclosed in WO 2012/092115)+TX, a molluscicide selected from the group of substances consisting of bis(tributyltin) oxide (IUPAC name) (913)+TX, bromoacetamide [CCN]+TX, calcium arsenate [CCN]+TX, cloethocarb (999)+TX, copper acetoarsenite [CCN]+TX, copper sulfate (172)+TX, fentin (347)+TX, ferric phosphate (IUPAC name) (352)+TX, metaldehyde (518)+TX, methiocarb (530)+TX, niclosamide (576)+TX, niclosamide-olamine (576)+TX, pentachlorophenol (623)+TX, sodium pentachlorophenoxide (623)+TX, tazimcarb (1412)+TX, thiodicarb (799)+TX, tributyltin oxide (913)+TX, trifenmorph (1454)+TX, trimethacarb (840)+TX, triphenyltin acetate (IUPAC name) (347) and triphenyltin hydroxide (IUPAC name) (347)+TX, pyriprole [394730-71-3]+TX, a nematicide selected from the group of substances consisting of AKD-3088 (compound code)+TX, 1,2-dibromo-3-chloropropane (IUPAC/Chemical Abstracts name) (1045)+TX, 1,2-dichloropropane (IUPAC/Chemical Abstracts name) (1062)+TX, 1,2-dichloropropane with 1,3-dichloropropene (IUPAC name) (1063)+TX, 1,3-dichloropropene (233)+TX, 3,4-dichlorotetrahydrothiophene 1,1-dioxide (IUPAC/Chemical Abstracts name) (1065)+TX, 3-(4-chlorophenyl)-5-methylrhodanine (IUPAC name) (980)+TX, 5-methyl-6-thioxo-1,3,5-thiadiazinan-3-ylacetic acid (IUPAC name) (1286)+TX, 6-isopentenylaminopurine (alternative name) (210)+TX, abamectin (1)+TX, acetoprole [CCN]+TX, alanycarb (15)+TX, aldicarb (16)+TX, aldoxycarb (863)+TX, AZ 60541 (compound code)+TX, benclothiaz [CCN]+TX, benomyl (62)+TX, butylpyridaben (alternative name)+TX, cadusafos (109)+TX, carbofuran (118)+TX, carbon disulfide (945)+TX, carbosulfan (119)+TX, chloropicrin (141)+TX, chlorpyrifos (145)+TX, cloethocarb (999)+TX, cytokinins (alternative name) (210)+TX, dazomet (216)+TX, DBCP (1045)+TX, DCIP (218)+TX, diamidafos (1044)+TX, dichlofenthion (1051)+TX, dicliphos (alternative name)+TX, dimethoate (262)+TX, doramectin (alternative name) [CCN]+TX, emamectin (291)+TX, emamectin benzoate (291)+TX, eprinomectin (alternative name) [CCN]+TX, ethoprophos (312)+TX, ethylene dibromide (316)+TX, fenamiphos (326)+TX, fenpyrad (alternative name)+TX, fensulfothion (1158)+TX, fosthiazate (408)+TX, fosthietan (1196)+TX, furfural (alternative name) [CCN]+TX, GY-81 (development code) (423)+TX, heterophos [CCN]+TX, iodomethane (IUPAC name) (542)+TX, isamidofos (1230)+TX, isazofos (1231)+TX, ivermectin (alternative name) [CCN]+TX, kinetin (alternative name) (210)+TX, mecarphon (1258)+TX, metam (519)+TX, metam-potassium (alternative name) (519)+TX, metam-sodium (519)+TX, methyl bromide (537)+TX, methyl isothiocyanate (543)+TX, milbemycin oxime (alternative name) [CCN]+TX, moxidectin (alternative name) [CCN]+TX, Myrothecium verrucaria composition (alternative name) (565)+TX, NC-184 (compound code)+TX, oxamyl (602)+TX, phorate (636)+TX, phosphamidon (639)+TX, phosphocarb [CCN]+TX, sebufos (alternative name)+TX, selamectin (alternative name) [CCN]+TX, spinosad (737)+TX, terbam (alternative name)+TX, terbufos (773)+TX, tetrachlorothiophene (IUPAC/Chemical Abstracts name) (1422)+TX, thiafenox (alternative name)+TX, thionazin (1434)+TX, triazophos (820)+TX, triazuron (alternative name)+TX, xylenols [CCN]+TX, YI-5302 (compound code) and zeatin (alternative name) (210)+TX, fluensulfone [318290-98-1]+TX, a nitrification inhibitor selected from the group of substances consisting of potassium ethylxanthate [CCN] and nitrapyrin (580)+TX, a plant activator selected from the group of substances consisting of acibenzolar (6)+TX, acibenzolar-S-methyl (6)+TX, probenazole (658) and *Reynoutria sachalinensis* extract (alternative name) (720)+TX, a synergist selected from the group of substances consisting of 2-(2-butoxyethoxy)ethyl piperonylate (IUPAC name) (934)+TX, 5-(1,3-benzodioxol-5-yl)-3-hexylcyclohex-2-enone (IUPAC name) (903)+TX, farnesol with nerolidol (alternative name) (324)+TX, MB-599 (development code) (498)+TX, MGK 264 (development code) (296)+TX, piperonyl butoxide (649)+TX, piprotal (1343)+TX, propyl isomer (1358)+TX, S421 (development code) (724)+TX, sesamex (1393)+TX, sesasmolin (1394) and sulfoxide (1406)+TX, and biologically active compounds selected from the group consisting of azaconazole (60207-31-0]+TX, bitertanol [70585-36-3]+TX, bromuconazole [116255-48-2]+TX, cyproconazole [94361-06-5]+TX, difenoconazole [119446-68-3]+TX, diniconazole [83657-24-3]+TX, epoxiconazole [106325-08-0]+TX, fenbuconazole [114369-43-6]+TX, fluquinconazole [136426-54-5]+TX, flusilazole [85509-19-9]+TX, flutriafol [76674-21-0]+TX, hexaconazole [79983-71-4]+TX, imazalil [35554-44-0]+TX, imibenconazole [86598-92-7]+TX, ipconazole [125225-28-7]+TX, metconazole [125116-23-6]+TX, myclobutanil [88671-89-0]+TX, pefurazoate [101903-30-4]+TX, penconazole [66246-88-6]+TX, prothioconazole [178928-70-6]+TX, pyrifenox [88283-41-4]+TX, prochloraz [67747-09-5]+TX, propiconazole [60207-90-1]+TX, simeconazole [149508-90-7]+TX, tebuconazole [107534-96-3]+TX, tetraconazole [112281-77-3]+TX, triadimefon [43121-43-3]+TX, triadimenol [55219-65-3]+TX, triflumizole [99387-89-0]+TX, triticonazole [131983-72-7]+TX, ancymidol [12771-68-5]+TX, fenarimol [60168-88-9]+TX, nuarimol [63284-71-9]+TX, bupirimate [41483-43-6]+TX, dimethirimol [5221-53-4]+TX, ethirimol [23947-60-6]+TX, dodemorph [1593-77-7]+TX, fenpropidine [67306-00-7]+TX, fenpropimorph [67564-91-4]+TX, spiroxamine [118134-30-8]+TX, tridemorph [81412-43-3]+TX, cyprodinil [121552-61-2]+TX, mepanipyrim [110235-47-7]+TX, pyrimethanil [53112-28-0]+TX, fenpiclonil [74738-17-3]+TX, fludioxonil [131341-86-1]+TX, benalaxyl [71626-11-4]+TX, furalaxyl [57646-30-7]+TX, metalaxyl [57837-19-1]+TX, R-metalaxyl [70630-17-0]+TX, ofurace [58810-48-3]+TX, oxadixyl [77732-09-3]+TX, benomyl [17804-35-2]+TX, carbendazim [10605-21-7]+TX, debacarb [62732-91-6]+TX, fuberidazole [3878-19-1]+TX, thiabendazole [148-79-8]+TX, chlozolinate [84332-86-5]+TX, dichlozoline [24201-58-9]+TX, iprodione [36734-19-7]+TX, myclozoline [54864-61-8]+TX, procymidone [32809-16-8]+TX, vinclozoline [50471-44-8]+TX, boscalid [188425-85-6]+TX, carboxin [5234-68-4]+TX, fenfuram [24691-80-3]+TX, flutolanil [66332-96-5]+TX, mepronil [55814-41-0]+TX, oxycarboxin [5259-88-1]+TX, penthiopyrad [183675-82-3]+TX, thifluzamide [130000-40-7]+TX, guazatine [108173-90-6]+TX, dodine [2439-10-3] [112-65-2] (free base)+TX, iminoctadine [13516-27-3]+TX, azoxystrobin [131860-33-8]+TX, dimoxystrobin [149961-52-4]+TX, enestroburin {Proc. BCPC, Int. Congr., Glasgow, 2003, 1, 93}+TX, fluoxastrobin [361377-29-9]+TX, kresoxim-methyl [143390-89-0]+TX, metominostrobin [133408-50-1]+TX, trifloxystrobin [141517-21-7]+TX, orysastrobin [248593-16-0]+TX, picoxystrobin [117428-22-5]+TX, pyraclostrobin [175013-18-0]+TX, ferbam [14484-64-1]+TX, mancozeb [8018-01-7]+TX, maneb [12427-38-2]+TX, metiram [9006-42-2]+TX, propineb [12071-83-9]+TX, thiram [137-26-8]+TX, zineb [12122-67-7]+TX, ziram [137-30-4]+TX, captafol [2425-06-1]+TX, captan [133-06-2]+TX, dichlofluanid [1085-98-9]+TX, fluoroimide [41205-21-4]+TX, folpet [133-07-3]+TX, tolylfluanid [731-27-1]+TX, bordeaux mixture [8011-63-0]+TX, copperhydroxid [20427-59-2]+TX, copperoxychlorid [1332-40-7]+TX, coppersulfat [7758-98-7]+TX, copperoxid [1317-39-1]+TX, mancopper [53988-93-5]+TX, oxine-copper [10380-28-6]+TX, dinocap [131-72-6]+TX, nitrothalisopropyl [10552-74-6]+TX, edifenphos [17109-49-8]+TX, iprobenphos [26087-47-8]+TX, isoprothiolane [50512-35-1]+TX, phosdiphen [36519-00-3]+TX, pyrazophos [13457-18-6]+TX, tolclofos-methyl [57018-04-9]+TX, acibenzolar-S-methyl [135158-54-2]+TX, anilazine [101-05-3]+TX, benthiavalicarb [413615-35-7]+TX, blasticidin-S [2079-00-7]+TX, chinomethionat [2439-01-2]+TX, chloroneb [2675-77-6]+TX, chlorothalonil [1897-45-6]+TX, cyflufenamid [180409-60-3]+TX, cymoxanil [57966-95-7]+TX, dichlone [117-80-6]+TX, diclocymet [139920-32-4]+TX, diclomezine [62865-36-5]+TX, dicloran [99-30-9]+TX, diethofencarb [87130-20-9]+TX, dimetho-morph [110488-70-5]+TX, SYP-L190 (Flumorph) [211867-47-9]+TX, dithianon [3347-22-6]+TX, ethaboxam [162650-77-3]+TX, etridiazole [2593-15-9]+TX, famoxadone [131807-57-3]+TX, fenamidone [161326-34-7]+TX, fenoxanil [115852-48-7]+TX, fentin [668-34-8]+TX, ferimzone [89269-64-7]+TX, fluazinam [79622-59-6]+TX, fluopicolide [239110-15-7]+TX, flusulfamide [106917-52-6]+TX, fenhexamid [126833-17-8]+TX, fosetyl-aluminium [39148-24-8]+TX, hymexazol [10004-44-1]+TX, iprovalicarb [140923-17-7]+TX, IKF-916 (Cyazofamid) [120116-88-3]+TX, kasugamycin [6980-18-3]+TX, methasulfocarb [66952-49-6]+TX, metrafenone [220899-03-6]+TX, pencycuron [66063-05-6]+TX, phthalide [27355-22-2]+TX, polyoxins [11113-80-7]+TX, probenazole [27605-76-1]+TX, propamocarb [25606-41-1]+TX, proquinazid [189278-12-4]+TX, pyroquilon [57369-32-1]+TX, quinoxyfen [124495-18-7]+TX, quintozene [82-68-8]+TX, sulfur [7704-34-9]+TX, tiadinil [223580-51-6]+TX, triazoxide [72459-58-6]+TX, tricyclazole [41814-78-2]+TX, triforine [26644-46-2]+TX, validamycin [37248-47-8]+TX, zoxamide (RH7281) [156052-68-5]+TX, mandipropamid [374726-62-2]+TX, isopyrazam [881685-58-1]+TX, sedaxane [874967-67-6]+TX, 3-difluoromethyl-1-methyl-1H-pyrazole-4-carboxylic acid (9-dichloromethylene-1,2,3,4-tetrahydro-1,4-methano-naphthalen-5-yl)-amide (disclosed in WO 2007/048556)+TX, 3-difluoromethyl-1-methyl-1H-pyrazole-4-carboxylic acid (3',4',5'-trifluoro-biphenyl-2-yl)-amide (disclosed in WO 2006/087343)+TX, [(3S,4R,4aR,6S,6aS,12R,12aS,12bS)-3-[(cyclopropylcarbonyl)oxy]-1,3,4,4a,5,6,6a,12,12a,12b-decahydro-6,12-dihydroxy-4,6a,12b-trimethyl-11-oxo-9-(3-pyridinyl)-2H,11Hnaphtho[2,1-b]pyrano[3,4-e]pyran-4-yl] methylcyclopropanecarboxylate [915972-17-7]+TX, benzovindiflupyr (solatenol)+TX, pydiflumetofen (adepidyn)+TX and 1,3,5-trimethyl-N-(2-methyl-1-oxopropyl)-N-[3-(2-methylpropyl)-4[2,2,2-trifluoro-1-methoxy-1-(trifluoromethyl)ethyl]phenyl]-1H-pyrazole-4-carboxamide [926914-55-8]+TX.

The references in brackets behind the active ingredients, e.g. [3878-19-1] refer to the Chemical Abstracts Registry number. The above described mixing partners are known. Where the active ingredients are included in "The Pesticide Manual" [The Pesticide Manual—A World Compendium; Thirteenth Edition; Editor: C. D. S. TomLin; The British Crop Protection Council], they are described therein under the entry number given in round brackets hereinabove for the particular compound; for example, the compound "abamectin" is described under entry number (1). Where "[CCN]" is added hereinabove to the particular compound, the compound in question is included in the "Compendium of Pesticide Common Names", which is accessible on the internet [A. Wood; *Compendium of Pesticide Common Names*, Copyright © 1995-2004]; for example, the compound "acetoprole" is described under the internet address http://www.alanwood.net/pesticides/acetoprole.html.

Most of the active ingredients described above are referred to hereinabove by a so-called "common name", the relevant "ISO common name" or another "common name" being used in individual cases. If the designation is not a "common name", the nature of the designation used instead is given in round brackets for the particular compound; in that case, the IUPAC name, the IUPAC/Chemical Abstracts name, a "chemical name", a "traditional name", a "compound name" or a "development code" is used or, if neither one of those designations nor a "common name" is used, an "alternative name" is employed. "CAS Reg. No" means the Chemical Abstracts Registry Number.

Suitable herbicides in compositions according to embodiments 16-17 include pinoxaden, bicyclopyrone, mesotrione, fomesafen, tralkoxydim, napropamide, amitraz, propanil, pyrimethanil, dicloran, tecnazene, toclofos methyl, flamprop M, 2,4-D, MCPA, mecoprop, clodinafop-propargyl, cyhalofop-butyl, diclofop methyl, haloxyfop, quizalofop-P, indol-3-ylacetic acid, 1-naphthylacetic acid, isoxaben, tebutam, chlorthal dimethyl, benomyl, benfuresate, dicamba, dichlobenil, benazolin, triazoxide, fluazuron, teflubenzuron, phenmedipham, acetochlor, alachlor, metolachlor, pretilachlor, thenylchlor, alloxydim, butroxydim, clethodim, cyclodim, sethoxydim, tepraloxydim, pendimethalin, dinoterb, bifenox, oxyfluorfen, acifluorfen, fluazifop, S-metolachlor, glyphosate, glufosinate, paraquat, diquat, fluoroglycofen-ethyl, bromoxynil, ioxynil, imazamethabenz-methyl, imazapyr, imazaquin, imazethapyr, imazapic, imazamox, flumioxazin, flumiclorac-pentyl, picloram, amodosulfuron, chlorsulfuron, nicosulfuron, rimsulfuron, triasulfuron, triallate, pebulate, prosulfocarb, molinate, atrazine, simazine, cyanazine, ametryn, prometryn, terbuthylazine, terbutryn, sulcotrione, isoproturon, linuron, fenuron, chlorotoluron, metoxuron, iodosulfuron, mesosulfuron, diflufenican, flufenacet, fluroxypyr, aminopyralid, pyroxsulam, XDE-848 Rinskor and halauxifen-methyl.

Suitable plant growth regulators in compositions according to embodiments 16-17 include paclobutrazole and 1-methylcyclopropene.

Suitable safeners in compositions according to embodiments 16-17 include benoxacor, cloquintocet-mexyl, cyometrinil, dichlormid, fenchlorazole-ethyl, fenclorim, flurazole, fluxofenim, mefenpyr-diethyl, MG-191, naphthalic anhydride and oxabetrinil.

Particular agrochemical active ingredients in compositions according to embodiments 16-17 are nicosulfuron, fomesafen, mesotrione, pinoxaden, cyantraniliprole, isopyrazam, epoxiconazole, pydiflumetofen and benzovindiflupyr.

The various editions of The Pesticide Manual (British Crop Production Council, especially 17$^{th}$ edition) also disclose details of agrochemicals, any one of which may suitably be used in compositions according to embodiments 16-17.

Generally any biologically active ingredient will be present at a concentration of from about 0.000001% to about 90% w/w; preferably from about 0.001% to about 90% w/w, in an agrochemical composition.

Agrochemical compositions of the invention may be in the form of a ready-to-use formulation or in concentrate form suitable for further dilution by the end user, and the concentration of agrochemical and compound according to any one embodiments 1-15 will be adjusted accordingly. In concentrated form, compositions of the invention typically contain an agrochemical at from 5 to 90% w/w, more preferably from 5 to 75% w/w, even more preferably from 10 to 50% w/w, of the total composition. Ready-to-use compositions of the invention will typically contain an agrochemical at from 0.000001% to 1% w/w, more preferably from 0.000001% to 0.5% w/w, and more preferably still from 0.001% to 0.1% w/w, of the total composition.

Typically a specific individual compound according to any one of embodiment 1-15 will have a concentration of from about 0.0005% to about 90% w/w of the total composition; preferably from about 0.05% to about 90% w/w. When in concentrated form, compositions of the invention typically contain a compound according to any one embodiments 1-15 at from 1% to 80% w/w, preferably from 5% to 60% w/w, more preferably from 5% w/w to 40% w/w and even more preferably from 5% w/w to 20% w/w of the total composition.

Ready to use compositions of the invention typically contain a compound according to any one embodiments 1-15 at from about 0.01% to about 2% w/w of the total composition, more preferably still from about 0.05% to about 1% w/w of the total composition. If the specific individual compound according to any one embodiments 1-15 is present with a blend of other compounds according to any one embodiments 1-15 due to a variety of values of n, then these concentration ranges for the individual compound may be varied such that the lower limit is reduced by a factor of 10 and the upper limit is reduced by a factor of 2.

Suitably, in a composition of the present invention, typically a compound according to any one embodiments 1-15 where n is an average value, will have a concentration of from about 0.0005% to about 90% w/w of the total composition; preferably from about 0.05% to about 90% w/w. When in concentrated form, compositions of the invention typically contain a compound according to any one embodiments 1-15 at from 1% to 80% w/w, preferably from 5% to 60% w/w, more preferably from 10% w/w to 40% w/w and even more preferably from 10% w/w to 20% w/w of the total composition. Ready to use compositions of the invention typically contain a compound according to any one embodiments 1-15 at from about 0.01% to about 2% w/w of the total composition, more preferably still from about 0.1% to about 1% w/w of the total composition.

Compounds according to any one of embodiments 1-15 may be formulated in a composition which also contains a biologically active ingredient (for example, an agrochemical) (this is often referred to as a built-in adjuvant formulation) or may be present in a separate composition which does not contain a biologically active ingredient but which is combined with a composition which contains a biologically active ingredient (for example when an end user, such as a farmer, separately adds both a formulation of a biologically active ingredient and a formulation of a compound according to any one embodiments 1-15 to a spray-tank of water, in which each formulation either dissolves or disperses prior to being sprayed by the farmer on his crops) (this is often referred to as a tank-mix adjuvant formulation).

Compositions of the invention may be formulated in any suitable manner known to the man skilled in the art. As mentioned above, in one form a composition of the invention is a formulation concentrate which may be diluted or dispersed (typically in water) by an end-user (typically a farmer) in a spray tank prior to application.

Additional formulation components may be formulated with a compound according to any one of embodiments 1-15 or with a composition according to the present invention. Such additional components include, for example, adjuvants, surfactants, emulsifiers and solvents; standard formulation publications disclose such formulation components suitable for use with the present invention (for example, Chemistry and Technology of Agrochemical Formulations, Ed. Alan Knowles, published by Kluwer Academic Publishers, The Netherlands in 1998; and Adjuvants and Additives: 2006 Edition by Alan Knowles, Agrow Report DS256, published by Informa UK Ltd, December 2006). Further standard formulation components suitable for use with the present invention are disclosed in WO2009/130281A1 (see from page 46, line 5 to page 51, line 40).

Thus, compositions of the present invention may also comprise one or more surfactants or dispersing agents to assist the emulsification of the biologically active ingredient on dispersion or dilution in an aqueous medium (dispersant system). The emulsification system is present primarily to assist in maintaining the emulsified biologically active ingredient in water. Many individual emulsifiers, surfactants and mixtures thereof suitable for forming an emulsion system for an agrochemical are known to those skilled in the art and a very wide range of choices is available. Typical surfactants that may be used to form an emulsifier system include those containing ethylene oxide, propylene oxide or both ethylene oxide and propylene oxide; aryl or alkylaryl sulphonates and combinations of these with either ethylene oxide or propylene oxide or both; carboxylates and combinations of these with either ethylene oxide or propylene oxide or both. Polymers and copolymers are also commonly used.

Compositions of the present invention may also include solvents, which may have a range of water solubilities. Oils with very low water solubilities may be added to the solvent of the present invention for assorted reasons such as the provision of scent, safening, cost reduction, improvement of emulsification properties and alteration of solubilising power. Solvents with higher water solubility may also be added for various reasons, for instance to alter the ease with which a formulation emulsifies in water, to improve the solubility of a pesticide (agrochemical) or of the other optional additives in the formulation, to change the viscosity of the formulation or to add a commercial benefit.

Other optional ingredients which may be added to the formulation include for example, colourants, scents and other materials which benefit a typical agrochemical formulation.

Compositions of the invention may formulated for example, as emulsion or dispersion concentrates, emulsions in water or oil, as a suspension of particles in an emulsion or oil, as microencapsulated formulations, aerosol sprays or fogging formulations; and these may be further formulated into granular materials or powders, for example for dry application or as water-dispersible formulations. Preferably compositions of the invention will be formulated as, or comprised by an emulsion concentrate (EC), an emulsion in water (EW), a suspension of particles in water (SC), a microcapsule formulation (CS), a soluble liquid (SL), a suspension of particles with an emulsion (SE), a dispersion concentrate (DC) or a suspension of particles in oil (OD).

Compositions of the invention may be used to control pests. The term "pest" as used herein includes insects, fungi, molluscs, nematodes and unwanted plants. Thus, in order to control a pest a composition of the invention may be applied directly to the pest, or to the locus of a pest.

Compositions of the invention also have utility in the seed treatment arena, and thus may be applied as appropriate to seeds.

In the description of the present invention above, the compounds according to any one of embodiments 1 to 15 are described as individual compounds (i.e. n and m have integral values, relating to a specific number of EO or PO units, respectively). Of course, typical alkoxylation reactions will provide a distribution of the number of EO and PO units rather than one single number of units. Therefore, in an alternative aspect of the present invention, there is provided a compound according to any one embodiments 1-15, a composition of said compound, methods of making and using said compositions and use of said compounds as herein described except the values of n and m are defined as an average value [which may be either the mean, the mode or the median value; all three may be very similar to one another] and where n may be integral or non-integral and is selected from 2 to 20 inclusive, particularly from 5 to 15; more particularly from 7 to 12; and where m may be integral or non-integral and is selected from 2 to 20 inclusive, particularly 2 to 15, more particularly 2 to 8.

Various aspects and embodiments of the present invention will now be illustrated in more detail by way of example. It will be appreciated that modification of detail may be made without departing from the scope of the invention.

EXPERIMENTAL

The following pyrimidine adjuvants have been prepared:

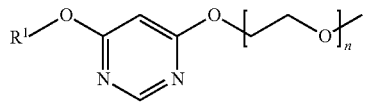

| Adjuvant | R1 | n |
|---|---|---|
| Adjuvant 1 | Hexyl | 2 |
| Adjuvant 2 | Hexyl | 10 |
| Adjuvant 3 | Hexyl | 20 |
| Adjuvant 4 | Nonyl | 7 |
| Adjuvant 5 | Nonyl | 10 |
| Adjuvant 6 | Dodecyl | 7 |
| Adjuvant 7 | Dodecyl | 10 |
| Adjuvant 8 | Hexadecyl | 10 |
| Adjuvant 9 | Oleyl | 2 |
| Adjuvant 10 | Oleyl | 10 |
| Adjuvant 11 | Oleyl | 20 |

| Adjuvant | R1 | m |
|---|---|---|
| Adjuvant 12 | Dodecyl | 3 |

As an example, adjuvant 10 was prepared as follows:

Step (a):

To a three necked round bottomed flask equipped with a nitrogen gas inlet, bubbler and thermoprobe, was added oleyl alcohol (48 g, 0.179 mol) followed by lithium tert-butoxide (1M in THF) (179 ml, 0.179 mol) and the reaction mixture stirred at room temperature for 30 minutes. A solution of 4,6-difluoropyrimidine (21 g, 0.179 mol) in anhydrous THF (80 mL) in a three necked round bottomed flask equipped with nitrogen gas inlet/bubbler and thermoprobe was cooled to 0° C. and the pre-mixed solution of oleyl alcohol and lithium tert-butoxide was added dropwise, keeping $T_{int}$<5° C. Once addition was complete, the solution was allowed to warm to room temperature over 2 hrs. Once the reaction was complete, water (500 ml) and EtOAc (500 ml) were added and the layers separated (brine required). The aqueous layer was extracted with EtOAc (2×500 ml). The combined organic layers were dried (MgSO$_4$), filtered and concentrated in vacuo to afford the product (63 g, 95%) as an orange liquid.

Step (b):

To a 2 L three necked round bottomed flask equipped with stirrer bar, dropping funnel, thermoprobe, N$_2$ inlet/bubbler and ice/water bath was added methoxypoly(ethylene glycol) (Carbowax 550™ MPEGs, average molecular weight of approximately 550, average number of oxyethylene units approximately 10, 50 g, 0.090 mol). Step (a) product (Step (a), 35 g, 0.095 mol) in DMSO (Stock, 400 ml) was added to the methoxypolyethylene glycol in one portion. A solution of potassium tert-butoxide (Stock, 10.7 g, 0.095 mol, 1.05 eq) in THF (Stock, 95 ml) (1M solution) was added in one go via a dropping funnel. The ice bath was removed and the reaction mixture stirred at room temperature over the weekend. The reaction mixture was cooled in an ice bath and water (400 ml) was added slowly dropwise over 15 minutes then extracted with EtOAc (3×400 ml). The combined organics were washed with water (600 ml) and dried (MgSO$_4$). The crude (60 g) was purified by column chromatography (load in petrol, 9.5×17 cm silica, 120 ml fractions, TLC in 5% MeOH/dichloromethane, KMnO$_4$ to visualize, gradient elution with EtOAc/petrol: 500 ml 30%, 1 L 50% 1 L dichloromethane then MeOH/dichloromethane: 1 L 2%, 1 L 4%, 1 L 6%, 2.5 L 8%) to afford the product (44 g mixed with DMSO). This was dissolved in dichloromethane (300 ml), washed with water (4×300 ml) and dried (MgSO$_4$) to afford the product (36 g) as a yellow/orange oil.

The other adjuvants have been prepared in a similar manner as adjuvant 10 using the appropriate reactants. For example, for adjuvants with 7 EO, Carbowax MPEG 350™ has been used, for adjuvants with 2 EO and 20 EO Methyl Carbitol™ and MPEG 1000™—Ineos/mPEG-OH, MW 1 k (Creative PEGworks) has been used, respectively. For adjuvants with 3 PO Dowanol TPM™ has been used.

The structure of the compounds were confirmed by NMR and liquid chromatography using the following conditions:

NMR:

Spectrometer: Bruker AvIII 400 MHz

Solvent: d4-methanol

Techniques: 1D 1H NMR, 2D 1H, 1H DQF-COSY 2D 1H, $^{13}$C HSQC, HMBC NMR

Adjuvant 10:

$^1$H NMR (400 MHz, d4-methanol) δ ppm 0.82-0.95 (m, 3H), 1.28 (br s, 17H), 1.39-1.49 (m, 2H), 1.68-1.83 (m, 2H), 3.35 (s, 3H), 3.49-3.55 (m, 2H), 3.57-3.70 (m, 23H), 3.82 (dd, J=5.40, 4.00 Hz, 2H), 4.29 (t, J=6.60 Hz, 2H), 4.40-4.50 (m, 2H), 6.15 (s, 1H), 8.35 (s, 1H).

Liquid Chromatography:

The samples were analyzed using liquid chromatography in conjunction with diode array detection (DAD), charged aerosol detection (CAD) and mass spectrometry (MS) as follows:

Sample Preparation:

All samples were prepared at either 0.1 mg mL−1 concentration (CAR1224B, CAR1495B, CAR1496A) or 1 mg mL−1 concentration (all other samples), in 90:10 Acetonitrile/H2O (vol/vol), before being transferred to auto-sampler vials. For each material, the same vial was used for the C18 Reverse-Phase and the Hydrophilic Interaction Liquid Chromatography (HILIC) experiments (as outlined below).

Chromatographic Conditions:

Analyses were performed using a Waters Acquity UPLC instrument. Detection was performed using a Waters photodiode array detector (PDA or DAD) (detection λ=240 or 254 nm), a Thermo Fisher Scientific Corona Veo RS charged aerosol detector (CAD), and a Waters SQ Detector 2 mass spectrometer (MS). Each sample was analysed by two different chromatographic methods:

(i) $C_{18}$ Reverse-Phase Liquid Chromatography

Column: Phenomenex $C_{18}$ Kinetex (100×3 mm, 2.6 μm particle size, serial no. H17-143356)

Temperature: 40° C.

Flow rate: 0.5 mL min$^{-1}$

Mobile Phase A: ASTM Type I water+100 mM ammonium acetate+2.5 mL L$^{-1}$ acetic acid (pH 5 approx.)

Mobile Phase B: acetonitrile+2.5 mL L$^{-1}$ acetic acid (pH 5)

Run time: 60 minutes

Mobile Phase Gradient:

| Time (mins) | | | | | | | | | |
|---|---|---|---|---|---|---|---|---|---|
| | 0 | 2 | 20 | 30 | 45 | 45.1 | 55 | 55.1 | 60 |
| % A | 85 | 85 | 20 | 10 | 10 | 0 | 0 | 85 | 85 |
| % B | 15 | 15 | 80 | 90 | 90 | 100 | 100 | 15 | 15 |

(ii) Hydrophilic Interaction Liquid Chromatography (HILIC)

Column: Waters BEH HILIC (150×2.1 mm, 1.7 μm particle size, serial no. 03003705818509)

Temperature: 30° C.

Flow rate: 0.45 mL min$^{-1}$

Mobile Phase A: 97:3 acetonitrile/H2O+300 mM ammonium acetate (vol/vol)

Mobile Phase B: 50:47:3 acetonitrile/H2O/H2O+300 mM ammonium acetate (vol/vol/vol)

Run time: 40 minutes

Mobile Phase Gradient:

| | Time (mins) | | | | | | |
|---|---|---|---|---|---|---|---|
| | 0 | 5 | 15 | 21 | 23 | 25 | 40 |
| % A | 100 | 100 | 70 | 0 | 0 | 100 | 100 |
| % B | 0 | 0 | 30 | 100 | 100 | 0 | 0 |

Interpretation of Data:

The most abundant ethoxylate (EO) or propoxylate (PO) number of each sample was determined according to the peak of highest integrated area in the CAD chromatogram of each HILIC experiment. The identity of this peak was confirmed by examining the corresponding mass spectrum (from the MS chromatogram).

Biological Data:

The compounds were tested for their ability to act as adjuvants for agrochemical compositions comprising the following pesticidal active ingredients:

Nicosulfuron

Fomesafen

Mesotrione

Pinoxaden

Cyantraniliprole

Isopyrazam

Epoxiconazole

Nicosulfuron Examples

The efficacy of adjuvants 1-12 as adjuvants for the herbicide nicosulfuron were tested in a glasshouse against four weed species sown into standard soil in pots and cultivated under controlled conditions in a glasshouse (at 24/18° C. day/night; 16 hours light; 65% humidity). Nicosulfuron was added to the spray tank as a standard WG (water dispersible granule) formulation.

The plants were sprayed with nicosulfuron (in the absence of an adjuvant) at rates of 15 and 60 grams of pesticide per hectare using a laboratory track sprayer which delivered the aqueous spray composition at a rate of 200 litres per hectare, using a flat fan nozzle (Teejet 11002VS) at 2 bar. The spray tests were also carried out using nicosulfuron in conjunction with adjuvants 1-12. The adjuvant was added to the spray solution at a rate of 0.2% v/v. All spray solutions also contained 12.5% v/v of iso-Propanol. The weed species and their BBCH growth stage at spraying were *Abutilon theophrasti* (ABUTH; growth stage 13), *Chenopodium album* (CHEAL; growth stage 13-14), *Digitaria sanguinalis* (DIGSA; growth stage 11), and *Setaria viridis* (SETVI; growth stage 13). Each spray test was replicated three times. The test plants were then grown in a glasshouse under controlled conditions (at 24/18° C. day/night; 16 hours light; 65% humidity) and watered twice a day. The efficacy of the herbicide was assessed visually and expressed as a percentage of the leaf area killed. Samples were assessed at a time period of 21 days following application. The results shown in Table 1 below are mean averages over the two rates of nicosulfuron, and the three replicates.

TABLE 1

Testing of adjuvant activities in Nicosulfuron compositions.

| | | Mean % Herbicidal Activity | | | | |
|---|---|---|---|---|---|---|
| Test | Adjuvant | ABUTH | CHEAL | DIGSA | SETVI | Average over all Species |
| 1 | Adjuvant 7 | 59 | 86 | 84 | 96 | 81 |
| 1 | No Adjuvant | 39 | 38 | 18 | 64 | 40 |
| 2 | Adjuvant 6 | 38 | 83 | 74 | 91 | 71 |
| 2 | Adjuvant 8 | 53 | 85 | 87 | 96 | 80 |
| 2 | No Adjuvant | 15 | 13 | 3 | 80 | 28 |
| 3 | Adjuvant 8 | 66 | 85 | 93 | 95 | 85 |
| 3 | No Adjuvant | 34 | 14 | 22 | 84 | 38 |
| 4 | Adjuvant 12 | 66 | 83 | 93 | 96 | 85 |
| 4 | Adjuvant 8 | 74 | 83 | 89 | 96 | 86 |
| 4 | Adjuvant 2 | 61 | 80 | 89 | 97 | 82 |
| 4 | Adjuvant 3 | 49 | 76 | 88 | 93 | 76 |
| 4 | Adjuvant 1 | 64 | 84 | 88 | 93 | 83 |
| 4 | Adjuvant 5 | 49 | 63 | 49 | 91 | 63 |
| 4 | Adjuvant 4 | 48 | 78 | 70 | 94 | 73 |
| 4 | Adjuvant 10 | 58 | 80 | 88 | 97 | 81 |
| 4 | Adjuvant 11 | 64 | 82 | 88 | 94 | 82 |
| 4 | Adjuvant 9 | 57 | 82 | 88 | 95 | 80 |
| 4 | No Adjuvant | 63 | 45 | 4 | 89 | 50 |

Fomesafen Examples

The efficacy of adjuvants 1-12 as adjuvants for the herbicide fomesafen (as the sodium salt) were tested in a glasshouse against four weed species, sown into standard soil in pots and cultivated under controlled conditions in a glasshouse (at 24/18° C. day/night; 16 hours light; 65% humidity). Fomesafen sodium salt was added to the spray tank as a standard SL (soluble concentrate) formulation.

The plants were sprayed with fomesafen (in the absence of an adjuvant) at rates of 100 and 200 grams of pesticide per hectare using a laboratory track sprayer which delivered the aqueous spray composition at a rate of 200 litres per hectare, using a flat fan nozzle (Teejet 11002VS) at 2 bar. The spray tests were also carried out using fomesafen in conjunction with adjuvants 1-12. Unless otherwise stated, the adjuvants were added to the spray solution at a rate of 0.2% v/v. All spray solutions also contained 12.5% v/v of iso-Propanol to normalise the retention of the sprays on the hydrophobic plant surfaces. The weed species and their BBCH growth stage at spraying were *Abutilon theophrasti* (ABUTH; growth stage 12-13), *Chenopodium album* (CHEAL; growth stage 15), *Ipomea hederacea* (IPOHE; growth stage 12), and *Setaria viridis* (SETVI; growth stage 14). Each spray test was replicated three times. The test plants were then grown in a glasshouse under controlled conditions (at 24/18° C. day/night; 16 hours light; 65% humidity) and watered twice a day.

The efficacy of the herbicide was assessed visually and expressed as a percentage of the leaf area killed. Samples were assessed at a time period of 21 days following application. The results shown in Table 2 below are mean averages over the two rates of fomesafen, the three replicates and the three replicates.

TABLE 2

Testing of adjuvant activities in Fomesafen compositions.

| | | Mean % Herbicidal Activity | | | | |
|---|---|---|---|---|---|---|
| Test | Adjuvant | ABUTH | CHEAL | IPOHE | SETVI | Average over all Species |
| 1 | Adjuvant 6 | 31 | 80 | 64 | 25 | 50 |
| 1 | Adjuvant 8 | 36 | 73 | 51 | 13 | 43 |
| 1 | Adjuvant 10 | 28 | 88 | 50 | 17 | 46 |
| 1 | No Adjuvant | 16 | 19 | 16 | 34 | 21 |
| 2 | Adjuvant 8 | 53 | 78 | 92 | 17 | 60 |
| 2 | No Adjuvant | 16 | 46 | 55 | 18 | 34 |
| 3 | Adjuvant 7 | 46 | 94 | 98 | 45 | 71 |
| 3 | No Adjuvant | 43 | 53 | 56 | 20 | 43 |
| 4 | Adjuvant 12 | 74 | 80 | 98 | 77 | 82 |
| 4 | Adjuvant 8 | 75 | 65 | 97 | 65 | 75 |
| 4 | Adjuvant 2 | 57 | 68 | 95 | 53 | 68 |
| 4 | Adjuvant 3 | 47 | 54 | 88 | 37 | 56 |
| 4 | Adjuvant 1 | 74 | 79 | 91 | 65 | 77 |
| 4 | Adjuvant 5 | 60 | 55 | 64 | 49 | 57 |
| 4 | Adjuvant 4 | 51 | 45 | 93 | 53 | 61 |
| 4 | Adjuvant 10 | 56 | 60 | 92 | 65 | 68 |
| 4 | No Adjuvant | 66 | 48 | 50 | 53 | 54 |
| 4 | Adjuvant 11 | 48 | 80 | 98 | 39 | 66 |
| 4 | Adjuvant 9 | 52 | 64 | 88 | 64 | 67 |

TABLE 3

Testing of adjuvant activities in Fomesafen compositions.

| | | Mean % Herbicidal Activity | | | | |
|---|---|---|---|---|---|---|
| Test | Adjuvant | BRAPP | COMBE | DIGSA | POLCO | Average over all Species |
| 1 | Adjuvant 7 | 68 | | 80 | 70 | 73 |
| 1 | No Adjuvant | 39 | | 47 | 65 | 50 |
| 2 | Adjuvant 6 | 53 | 83 | 83 | 84 | 76 |
| 2 | Adjuvant 8 | 61 | 85 | 84 | 82 | 78 |
| 2 | No Adjuvant | 12 | 60 | 43 | 19 | 33 |
| 3 | Adjuvant 12 | 69 | | 84 | 98 | 84 |
| 3 | Adjuvant 8 | 64 | | 81 | 92 | 79 |
| 3 | Adjuvant 2 | 52 | | 79 | 94 | 75 |
| 3 | Adjuvant 3 | 38 | | 83 | 92 | 71 |
| 3 | Adjuvant 1 | 53 | | 81 | 81 | 72 |
| 3 | Adjuvant 5 | 48 | | 72 | 94 | 71 |
| 3 | Adjuvant 4 | 43 | | 83 | 93 | 73 |
| 3 | Adjuvant 10 | 61 | | 84 | 95 | 80 |
| 3 | No Adjuvant | 36 | | 45 | 80 | 54 |
| 3 | Adjuvant 11 | 58 | | 83 | 92 | 78 |
| 3 | Adjuvant 9 | 69 | | 82 | 92 | 81 |

| | | Mean % Herbicidal Activity | | | | |
|---|---|---|---|---|---|---|
| Test | Adjuvant | BRAPL | COMBE | DIGSA | POLCO | Average over all Species |
| 4 | Adjuvant 8 | 33 | 79 | 83 | 93 | 72 |
| 4 | No Adjuvant | 6 | 46 | 26 | 78 | 39 |

Mesotrione Examples

The efficacy of adjuvants 1-12 as an adjuvant for the herbicide mesotrione was tested in a glasshouse against four weed species sown into standard soil in pots and cultivated under controlled conditions in a glasshouse (at 24/18° C. day/night; 16 hours light; 65% humidity). Mesotrione was added to the spray tank as a standard SC (suspension concentrate) formulation.

The plants were sprayed with mesotrione (in the absence of an adjuvant) at rates of 30 and 60 grams of pesticide per hectare using a laboratory track sprayer which delivered the aqueous spray composition at a rate of 200 litres per hectare, using a flat fan nozzle (Teejet 11002VS) and an application volume of 200 litre/ha (at 2 bar). The spray tests were also carried out using mesotrione in conjunction with adjuvants 1-12. The adjuvants were added to the spray solution at a rate of 0.2% v/v unless otherwise stated. All spray solutions also contained 10% w/w of iso-Propanol. The weed species and their BBCH growth stage at spraying were *Brachiaria platyphylla* (BRAPP; growth stage 13-14) or *Brachiaria plantaginea* (BRAPL; growth stage 13-14), *Commelina benghalensis* (COMBE; growth stage 13), *Digitaria sanguinalis* (DIGSA; growth stage 14), and *Polygonum convolvulus* (POLCO; growth stage 13-14). Each spray test was replicated three times.

The test plants were then grown in a glasshouse under controlled conditions (at 24/18° C. day/night; 16 hours light; 65% humidity) and watered twice a day. The efficacy of the herbicide was assessed visually and expressed as a percentage of the leaf area killed. Samples were assessed at a time period of 21 days following application. The results shown in Table 3 below are mean averages over the two rates of mesotrione and the three replicates.

Pinoxaden Examples

The efficacy of adjuvants 1-12 as adjuvants for the herbicide pinoxaden were tested in a glasshouse against four weed species, sown into standard soil in pots and cultivated under controlled conditions in a glasshouse (at 20/16° C. day/night; 16 hours light; 65% humidity). Pinoxaden was added to the spray tank as a standard EC (emulsifiable concentrate) formulation.

The plants were sprayed with pinoxaden (in the absence of an adjuvant) at rates of 7.5 and 15 grams of pesticide per hectare using a laboratory track sprayer which delivered the aqueous spray composition at a rate of 200 litres per hectare, using a flat fan nozzle (Teejet 11002VS) at 2 bar. The spray tests were also carried out using pinoxaden in conjunction with adjuvants 1-12. The adjuvants were added to the spray solution at a rate of 0.2% v/v unless otherwise stated. All spray solutions also contained 10% w/w of iso-Propanol. The weed species and their BBCH growth stage at spraying were *Avena fatua* (AVEFA; growth stage 12), *Lolium perenne* (LOLPE; growth stage 13), *Alopecurus myosuroides* (ALOMY; growth stage 13), and *Setaria viridis* (SETVI; growth stage 13-14). Each spray test was replicated three times. The test plants were then grown in a glasshouse under controlled conditions (at 20/16° C. day/night; 16 hours light; 65% humidity) and watered twice a day. The efficacy of the herbicide was assessed visually and expressed as a percentage of the leaf area killed. Samples were assessed at a time period of 21 days following application. The results shown in Table 4 below are mean averages over the two rates of pinoxaden, and the three replicates.

TABLE 4

Testing of adjuvant activities in Pinoxaden compositions.

| Test | Adjuvant | Mean % Herbicidal Activity | | | | Average over all Species |
|---|---|---|---|---|---|---|
| | | ALOMY | AVEFA | LOLPE | SETVI | |
| 1 | Adjuvant 7 | 63 | 98 | 78 | 97 | 84 |
| 1 | No Adjuvant | 14 | 25 | 10 | 18 | 17 |
| 2 | Adjuvant 6 | 23 | 82 | 62 | 87 | 63 |
| 2 | Adjuvant 8 | 22 | 84 | 73 | 89 | 67 |
| 2 | No Adjuvant | 1 | 0 | 2 | 2 | 1 |
| 3 | Adjuvant 8 | 2 | 94 | 87 | 94 | 69 |
| 3 | No Adjuvant | 4 | 48 | 7 | 36 | 24 |
| 4 | Adjuvant 12 | 23 | 87 | 76 | 94 | 70 |
| 4 | Adjuvant 8 | 15 | 78 | 42 | 88 | 56 |
| 4 | Adjuvant 2 | 16 | 56 | 28 | 87 | 47 |
| 4 | Adjuvant 3 | 15 | 52 | 22 | 88 | 44 |
| 4 | Adjuvant 1 | 20 | 78 | 41 | 82 | 55 |
| 4 | Adjuvant 5 | 10 | 69 | 21 | 63 | 41 |
| 4 | Adjuvant 4 | 18 | 78 | 30 | 82 | 52 |
| 4 | Adjuvant 10 | 9 | 80 | 25 | 89 | 50 |
| 4 | Adjuvant 11 | 11 | 41 | 15 | 84 | 38 |
| 4 | Adjuvant 9 | 17 | 83 | 40 | 91 | 58 |
| 4 | No Adjuvant | 3 | 9 | 4 | 9 | 6 |

Cyantraniliprole Example

The efficacy of adjuvants 6, 7, 8 and 10 as adjuvants in compositions containing cyantraniliprole was tested in an aphid/French bean assay. The underside of two week old French bean (*Phaseolus vulgaris*) plants were infested with an aphid population *Aphis craccivora* of mixed ages contained in clip cages. One day after infestation, the tops of the plants were treated with a diluted suspension concentrate of the insecticide cyantraniliprole at rates of 3.125, 6.25, 12.5, 25, 50 mg of the insecticide per litre of spray solution, using a top-down laboratory track sprayer, which delivered the spray rate of 200 litres per hectare, using a flat fan nozzle (LU 90-01) at 2 bar. Spray tests were also carried out with a diluted suspension concentrate additionally comprising adjuvants 6, 7, 8 and 10 added to the spray solution at rates of 0.1 and/or 0.2% v/v, based on the quantity of spray liquor. The plants were incubated in the greenhouse for 5 days and the mortality evaluated for the mixed population of aphids. Each experiment was replicated twice and the results were averaged. Table 5 summarizes the results.

TABLE 5

Testing of adjuvant activities in Cyantraniliprole compositions.

| Adjuvant | Adjuvant Rate % v/v | Mean(% MORTALITY) |
|---|---|---|
| Adjuvant 7 | 0.2 | 66.1 |
| Adjuvant 6 | 0.2 | 68.5 |
| Adjuvant 8 | 0.1 | 62.1 |
| Adjuvant 8 | 0.2 | 60.8 |
| No Adjuvant | 0 | 0 |
| Adjuvant 10 | 0.1 | 49.8 |
| Adjuvant 10 | 0.2 | 70.2 |

Isopyrazam Example

Adjuvants 6, 7, 8 and 10 were tested as adjuvants for agrochemical compositions comprising isopyrazam.

Two week old wheat plants were inoculated with the fungus *Septoria tritici*. Four days after inoculation, the plants were sprayed with a diluted suspension concentrate formulation of the fungicide isopyrazam at rates of 6.5, 16, 40 and 100 mg of the fungicide per litre of spray solution, using a laboratory track sprayer which delivered the spray at a rate of 200 litres per hectare, using a flat fan nozzle (LU 90-01) at 2 bar. All spray solutions also contained 10% v/v of iso-Propanol. The leaves of the plants were assessed visually 17-18 days after infection and the damage was expressed as the percentage of the leaf area infected. Each spray test was replicated four times across the four application rates.

The results shown in Table 6 below are mean averages over the four rates of isopyrazam and the four replicates.

TABLE 6

Testing of adjuvant activities in Isopyrazam compositions.

| Test | Adjuvant | Disease Damage Mean |
|---|---|---|
| 1 | Adjuvant 7 | 12 |
| 1 | Adjuvant 6 | 9 |
| 1 | No adjuvant | 65 |
| 2 | Adjuvant 6 | 12 |
| 2 | Adjuvant 8 | 20 |
| 2 | No adjuvant | 74 |
| 2 | Adjuvant 10 | 17 |
| 3 | Adjuvant 6 | 7 |
| 3 | No adjuvant | 93 |
| 3 | Adjuvant 10 | 14 |

Epoxiconazole Examples

Adjuvants 6, 7, 8 and 10 were tested as adjuvants for agrochemical compositions comprising epoxiconazole.

Two week old wheat plants were inoculated with the fungus *Septoria tritici*. Four days after inoculation, the plants were sprayed with a diluted suspension concentrate formulation of the fungicide epoxiconazole at rates of 1.5, 4, 8.5 and 20 mg of the fungicide per litre of spray solution, using a laboratory track sprayer which delivered the spray at a rate of 200 litres per hectare, using a flat fan nozzle (LU 90-01) at 2 bar. Spray tests were also carried out with a diluted suspension concentrate additionally comprising the adjuvants 6, 7, 8 and 10 added to the spray solution at a rate of 0.1% v/v, based on the quantity of spray liquor. All spray solutions also contained 10% v/v of iso-Propanol. The leaves of the plants were assessed visually 17-18 days after infection and the damage was expressed as the percentage of the leaf area infected. Each spray test was replicated four times across the four application rates and the results are shown in Table 7.

TABLE 7

Testing of adjuvant activities in epoxyconazole compositions.

| Test | Adjuvant | Disease Damage Mean |
|---|---|---|
| 1 | Adjuvant 7 | 12 |
| 1 | Adjuvant 6 | 10 |
| 1 | No Adjuvant | 81 |
| 2 | Adjuvant 6 | 21 |
| 2 | Adjuvant 8 | 36 |
| 2 | No Adjuvant | 86 |
| 2 | Adjuvant 10 | 26 |
| 3 | Adjuvant 6 | 42 |
| 3 | No Adjuvant | 93 |

What is claimed is:

1. A compound of formula (I), or a salt thereof,

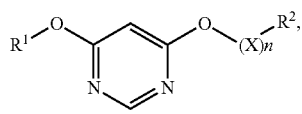
(I)

wherein
R¹ is selected from $C_4$-$C_{20}$-alkyl and $C_4$-$C_{20}$-alkenyl;
R² is selected from H, methyl, ethyl, n-propyl, isopropyl, n-butyl, isobutyl, s-butyl and t-butyl;
X is either

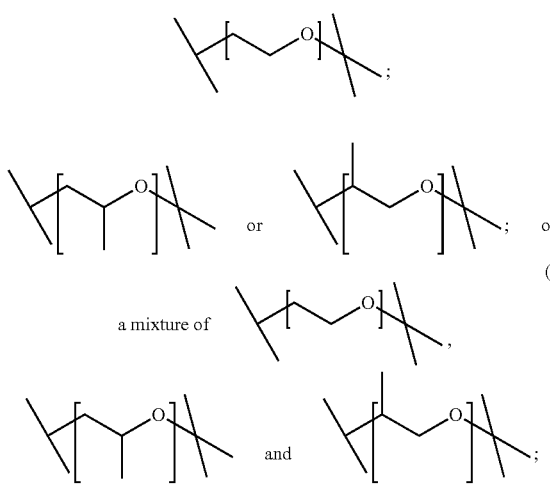

n is from 2 to 30.

2. A compound or salt according to claim 1, wherein X is

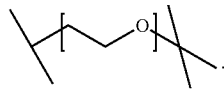

3. A compound or salt according to claim 1, wherein X is

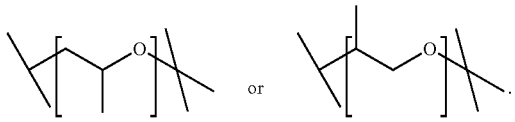

4. A compound or salt of claim 1 of formula (I)

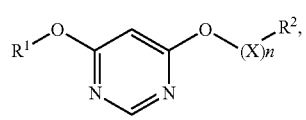
(I)

wherein
R¹ is selected from $C_6$-$C_{18}$-alkyl and $C_6$-$C_{18}$-alkenyl;
X is

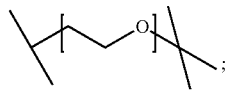

n is from 2 to 20;
R² is methyl or H.

5. A compound or salt according to claim 4 wherein R² is methyl and R¹ and n are as defined in the table

| Compound | R¹ | n |
|---|---|---|
| 1 | Hexyl | 2 |
| 2 | Hexyl | 10 |
| 3 | Hexyl | 20 |
| 4 | Nonyl | 7 |
| 5 | Nonyl | 10 |
| 6 | Dodecyl | 7 |
| 7 | Dodecyl | 10 |
| 8 | Hexadecyl | 10 |
| 9 | Oleyl | 2 |
| 10 | Oleyl | 10 |
| 11 | Oleyl | 20. |

6. A compound of claim 1 of formula (I)

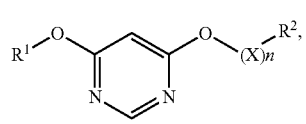
(I)

wherein
R¹ is selected from $C_6$-$C_{18}$-alkyl and $C_6$-$C_{18}$-alkenyl;
X is

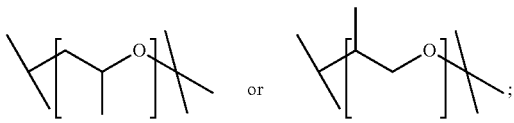 or ;

n is from 2 to 8;
R² is methyl or H.

7. A compound of claim 6 wherein R² is methyl, R¹ is dodecyl and n is 3.

8. A composition comprising a biologically active ingredient, particularly an agrochemical active ingredient, and a compound according to claim 1.

9. A tank-mix formulation comprising a compound according to claim 1.

10. A method of controlling pests comprising applying the agrochemical composition of claim 8 to said pests or to a locus of said pests.

11. A method of making an agrochemical composition according to claim 8, comprising combining a biologically active ingredient and a compound of formula (I), or a salt thereof,

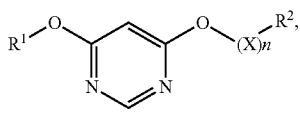 (I)

Wherein
R¹ is selected from $C_4$-$C_{20}$-alkyl and $C_4$-$C_{20}$-alkenyl;
R² is selected from H, methyl, ethyl, n-propyl, isopropyl, n-butyl, isobutyl, s-butyl and t-butyl;
X is either

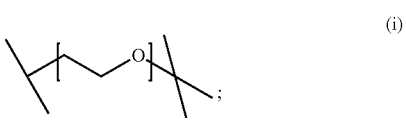 (i)

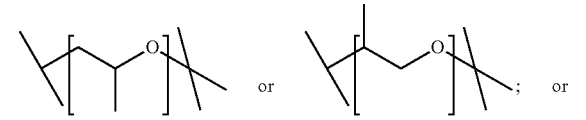 (ii)

or a mixture of 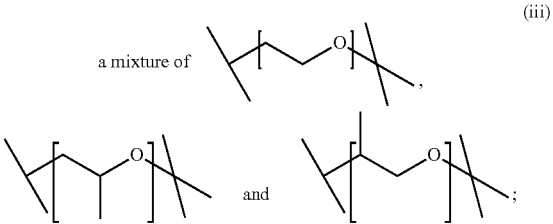 (iii)

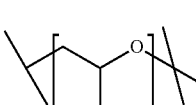 and 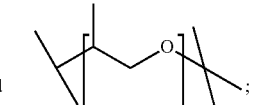 ;

n is from 2 to 30.

12. A composition comprising a biologically active ingredient and a compound according to claim 1, wherein the compound acts as an adjuvant in the composition.

13. The composition of claim 12 wherein the biologically active ingredient is an agrochemical active ingredient.

* * * * *